(12) United States Patent
Boyle et al.

(10) Patent No.: US 6,284,485 B1
(45) Date of Patent: Sep. 4, 2001

(54) NUCLEIC ACIDS ENCODING OSTEOPROTEGERIN

(75) Inventors: William J. Boyle, Moorpark; David L. Lacey, Thousand Oaks; Frank J. Calzone, Westlake Village; Ming-Shi Chang, Newbury Park, all of CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/795,445

(22) Filed: Feb. 6, 1997

Related U.S. Application Data

(62) Division of application No. 08/577,788, filed on Dec. 22, 1995.

(51) Int. Cl.$^7$ ................. C12N 1/21; C12N 5/10; C12N 15/12; C12N 15/63
(52) U.S. Cl. ............ 435/69.1; 435/69.4; 435/69.5; 435/325; 435/357; 435/358; 435/360; 435/365; 435/365.1; 435/364; 435/371; 435/252.3; 435/320.1; 536/23.5; 536/23.51
(58) Field of Search ................. 536/23.5, 23.51; 435/69.1, 69.5, 252.3, 320.1, 7.1, 325, 357, 358, 360, 365, 365.1, 364, 371, 69.4; 514/2; 530/300, 350

(56) References Cited

FOREIGN PATENT DOCUMENTS

| 7-054977 | 2/1995 | (JP) . |
| 7-207508 | 7/1995 | (JP) . |
| WO 96/28546 | 9/1996 | (WO) . |

OTHER PUBLICATIONS

Adams et al. Science 252: 1651–1656 (1991).
Beutler et al. Ann. Rev. Biochem, 57, 505–518 (1988).
Brinster et al. PNAS USA 82, 4438–4442 (1985).
Capon et al. Nature 337, 525–531 (1989).
Chen et al. Chemistry 270, 2874–2878 (1995).
Chomczynski and Sacchi Anal. Biochem, 162, 156–159, (1987).
Fisher et al. Cell 81. 935–946 (1995).
Gennaro, *Remington's Pharmaceutical Sciences,* 18th ed., Mack Publishing (1990).
Goeddel et al. Cold Spring Harbor Symp. Quart. Biol. LI, 597–609 (1986).
Goeddel, *Methods of Enzymology* v. 185, Academic Press (1990).
Gribskov et al. PNAS USA 84, 4355–4358 (1987).
Harlow and Lane *Antibodies: A Laboratory Manual* Cold Spring Harbor Laboratory Press, Cold Spring Harbor N.Y. (1988).
Kohno et al. PNAS USA 87, 8331–8335 (1990).
Loetscher et al. Cancer Cells 3(6), 221–226 (1991).
Luethy et al. Protein Science 3, 139–146 (1994).
MacDonald et al. Meth. Enzymol. 152, 219 (1987).
Nagata et al. Science 267, 1449–1456 (1995).
Ogden et al. Meth. Enzymol 152, 61 (1987).
Pearson et al., Meth. Enzymol. 183, 63 (1990).
Simonet et al. J. Clin. Invest. 94 1310–1319 (1994).
Smith et al. Cell 76, 959–962 (1994).
Suda et al. Cell 75, 1169–1178 (1993).

*Primary Examiner*—Elizabeth Kemmerer
*Assistant Examiner*—Regina M. DeBerry
(74) *Attorney, Agent, or Firm*—Robert B. Winter; Steven M. Odre; Ron K. Levy

(57) ABSTRACT

The present invention discloses a novel secreted polypeptide, termed Osteoprotegerin, which is a member of the tumor necrosis factor receptor superfamily and is involved in the regulation of bone metabolism. Also disclosed are nucleic acids encoding Osteoprotegerin, polypeptides, recombinant vectors and host cells for expression, antibodies which bind Osteoprotegerin, and pharmaceutical compositions. The polypeptides are used to treat bone diseases characterized by increased resorption such as osteoporosis.

16 Claims, 26 Drawing Sheets

FIG.1A

```
       148        178        208        238        268        298
FRI-1  ALLVFLDIIEWTTQETFPPKYLHYDPETGRQLLCDKCAPGTYLKQHCTVRRKTLCVPCPD
       :  :  ::::  ::  ::  :::::  ::  :  ::  ::::
SW:TNR2_HUMAN HALPAQVAFTPYAPEPGSTCRLREYYDQTAQMCCSKCSPGQHAKVFCTKTSDTVCDSCED
                30         40         50         60         70         80

328
FRI-1  YSYTDSWHTS
       :::  :  :
SW:TNR2_HUMAN STYTQLWNWVPECLSCGSRCSSDQVETQACTREQNRICTCRPGWYCALSKQEGCRLCAPL
                90        100        110        120        130        140
```

FIG.1B

```
FRI-1        69  YLHYDPETGRQLLCDKCAPGTYLKQHC.TVRRKTLCV.PCPDY.SYTDSW
                 |  :  ...  :  ::::  :  ::  . :  ::  ||  ::  ::  ||  .
TNFR profile 6   YHYYDQNGRMCEECHMCQPGHFLVKHCKQPKRDTVCHKPCEPGVTYTDDW FRI-1        116 H
                 —
TNFR profile 56  H
```

Z Score = 8.29

FIG. 2A

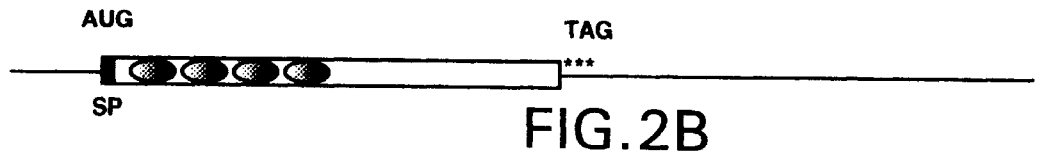

FIG. 2B

```
         10                  30                  50
ATCAAAGGCAGGGCATACTTCCTGTTGCCCAGACCTTATATAAAACGTCATGTTCGCCTG
         70                  90                 110
GGCAGCAGAGAAGCACCTAGCACTGGCCCAGCGGCTGCCGCCTGAGGTTTCCAGAGGACC
        130                 150                 170
ACAATGAACAAGTGGCTGTGCTGTGCACTCCTGGTGTTCTTGGACATCATTGAATGGACA
     M  N  K  W  L  C  C  A  L  L  V  F  L  D  I  I  E  W  T
        190                 210                 230
ACCCAGGAAACCTTTCCTCCAAAATACTTGCATTATGACCCAGAAACCGGACGTCAGCTC
  T  Q  E  T  F  P  P  K  Y  L  H  Y  D  P  E  T  G  R  Q  L
        250                 270                 290
TTGTGTGACAAATGTGCTCCTGGCACCTACCTAAAACAGCACTGCACAGTCAGGAGGAAG
  L  C  D  K  C  A  P  G  T  Y  L  K  Q  H  C  T  V  R  R  K
        310                 330                 350
ACACTGTGTGTCCCTTGCCCTGACTACTCTTATACAGACAGCTGGCACACGAGTGATGAA
  T  L  C  V  P  C  P  D  Y  S  Y  T  D  S  W  H  T  S  D  E
        370                 390                 410
TGCGTGTACTGCAGCCCCGTGTGCAAGGAACTGCAGACCGTGAAACAGGAGTGCAACCGC
  C  V  Y  C  S  P  V  C  K  E  L  Q  T  V  K  Q  E  C  N  R
        430                 450                 470
ACCCACAACCGAGTGTGCGAATGTGAGGAAGGGCGCTACCTGGAGCTCGAATTCTGCTTG
  T  H  N  R  V  C  E  C  E  E  G  R  Y  L  E  L  E  F  C  L
        490                 510                 530
AAGCACCGGAGCTGTCCCCCAGGCTTGGGTGTGCTGCAGGCTGGGACCCCAGAGCGAAAC
  K  H  R  S  C  P  P  G  L  G  V  L  Q  A  G  T  P  E  R  N
        550                 570                 590
ACGGTTTGCAAAAGATGTCCGGATGGGTTCTTCTCAGGTGAGACGTCATCGAAAGCACCC
  T  V  C  K  R  C  P  D  G  F  F  S  G  E  T  S  S  K  A  P
        610                 630                 650
TGTAGGAAACACACCAACTGCAGCTCACTTGGCCTCCTGCTAATTCAGAAAGGAAATGCA
  C  R  K  H  T  N  C  S  S  L  G  L  L  L  I  Q  K  G  N  A
        670                 690                 710
ACACATGACAATGTATGTTCCGGAAACAGAGAAGCAACTCAAAATTGTGGAATAGATGTC
  T  H  D  N  V  C  S  G  N  R  E  A  T  Q  N  C  G  I  D  V
        730                 750                 770
ACCCTGTGCGAAGAGGCATTCTTCAGGTTTGCTGTGCCTACCAAGATTATACCGAATTGG
  T  L  C  E  E  A  F  F  R  F  A  V  P  T  K  I  I  P  N  W
        790                 810                 830
CTGAGTGTTCTGGTGGACAGTTTGCCTGGGACCAAAGTGAATGCAGAGAGTGTAGAGAGG
  L  S  V  L  V  D  S  L  P  G  T  K  V  N  A  E  S  V  E  R
        850                 870                 890
ATAAAACGGAGACACAGCTCGCAAGAGCAAACTTTCCAGCTACTTAAGCTGTGGAAGCAT
  I  K  R  R  H  S  S  Q  E  Q  T  F  Q  L  L  K  L  W  K  H
        910                 930                 950
CAAAACAGAGACCAGGAAATGGTGAAGAAGATCATCCAAGACATTGACCTCTGTGAAAGC
  Q  N  R  D  Q  E  M  V  K  K  I  I  Q  D  I  D  L  C  E  S
        970                 990                1010
AGTGTGCAACGGCATATCGGCCACGCGAACCTCACCACAGAGCAGCTCCGCATCTTGATG
  S  V  Q  R  H  I  G  H  A  N  L  T  T  E  Q  L  R  I  L  M
```

FIG. 2C

```
        1030                  1050                  1070
GAGAGCTTGCCTGGGAAGAAGATCAGCCCAGACGAGATTGAGAGAACGAGAAAGACCTGC
 E  S  L  P  G  K  K  I  S  P  D  E  I  E  R  T  R  K  T  C
        1090                  1110                  1130
AAACCCAGCGAGCAGCTCCTGAAGCTACTGAGCTTGTGGAGGATCAAAAATGGAGACCAA
 K  P  S  E  Q  L  L  K  L  L  S  L  W  R  I  K  N  G  D  Q
        1150                  1170                  1190
GACACCTTGAAGGGCCTGATGTACGCACTCAAGCACTTGAAAGCATACCACTTTCCCAAA
 D  T  L  K  G  L  M  Y  A  L  K  H  L  K  A  Y  H  F  P  K
        1210                  1230                  1250
ACCGTCACCCACAGTCTGAGGAAGACCATCAGGTTCTTGCACAGCTTCACCATGTACCGA
 T  V  T  H  S  L  R  K  T  I  R  F  L  H  S  F  T  M  Y  R
        1270                  1290                  1310
TTGTATCAGAAACTCTTTCTAGAAATGATAGGGAATCAGGTTCAATCAGTGAAGATAAGC
 L  Y  Q  K  L  F  L  E  M  I  G  N  Q  V  Q  S  V  K  I  S
        1330                  1350                  1370
TGCTTATAGTTAGGAATGGTCACTGGGCTGTTTCTTCAGGATGGGCCAACACTGATGGAG
 C  L
        1390                  1410                  1430
CAGATGGCTGCTTCTCCGGCTCTTGAAATGGCAGTTGATTCCTTTCTCATCAGTTGGTGG
        1450                  1470                  1490
GAATGAAGATCCTCCAGCCCAACACACACACTGGGGAGTCTGAGTCAGGAGAGTGAGGCA
        1510                  1530                  1550
GGCTATTTGATAATTGTGCAAAGCTGCCAGGTGTACACCTAGAAAGTCAAGCACCCTGAG
        1570                  1590                  1610
AAAGAGGATATTTTTATAACCTCAAACATAGGCCCTTTCCTTCCTCTCCTTATGGATGAG
        1630                  1650                  1670
TACTCAGAAGGCTTCTACTATCTTCTGTGTCATCCCTAGATGAAGGCCTCTTTTATTTAT
        1690                  1710                  1730
TTTTTTATTCTTTTTTTCGGAGCTGGGGACCGAACCCAGGGCCTTGCGCTTGCGAGGCAA
        1750                  1770                  1790
GTGCTCTACCACTGAGCTAAATCTCCAACCCCTGAAGGCCTCTTTCTTTCTGCCTCTGAT
        1810                  1830                  1850
AGTCTATGACATTCTTTTTTCTACAATTCGTATCAGGTGCACGAGCCTTATCCCATTTGT
        1870                  1890                  1910
AGGTTTCTAGGCAAGTTGACCGTTAGCTATTTTTCCCTCTGAAGATTTGATTCGAGTTGC
        1930                  1950                  1970
AGACTTGGCTAGACAAGCAGGGGTAGGTTATGGTAGTTTATTTAACAGACTGCCACCAGG
        1990                  2010                  2030
AGTCCAGTGTTTCTTGTTCCTCTGTAGTTGTACCTAAGCTGACTCCAAGTACATTTAGTA
        2050                  2070                  2090
TGAAAAATAATCAACAAATTTTATTCCTTCTATCAACATTGGCTAGCTTTGTTTCAGGGC
        2110                  2130                  2150
ACTAAAAGAAACTACTATATGGAGAAAGAATTGATATTGCCCCCAACGTTCAACAACCCA
        2170                  2190                  2210
ATAGTTTATCCAGCTGTCATGCCTGGTTCAGTGTCTACTGACTATGCGCCCTCTTATTAC
        2230                  2250                  2270
TGCATGCAGTAATTCAACTGGAAATAGTAATAATAATAGAAATAAAATCTAGACTCC
        2290                  2310                  2330
ATTGGATCTCTCTGAATATGGGAATATCTAACTTAAGAAGCTTTGAGATTTCAGTTGTGT
        2350                  2370                  2390
TAAAGGCTTTTATTAAAAAGCTGATGCTCTTCTGTAAAAGTTACTAATATATCTGTAAGA
        2410                  2430
CTATTACAGTATTGCTATTTATATCCATCCAG
```

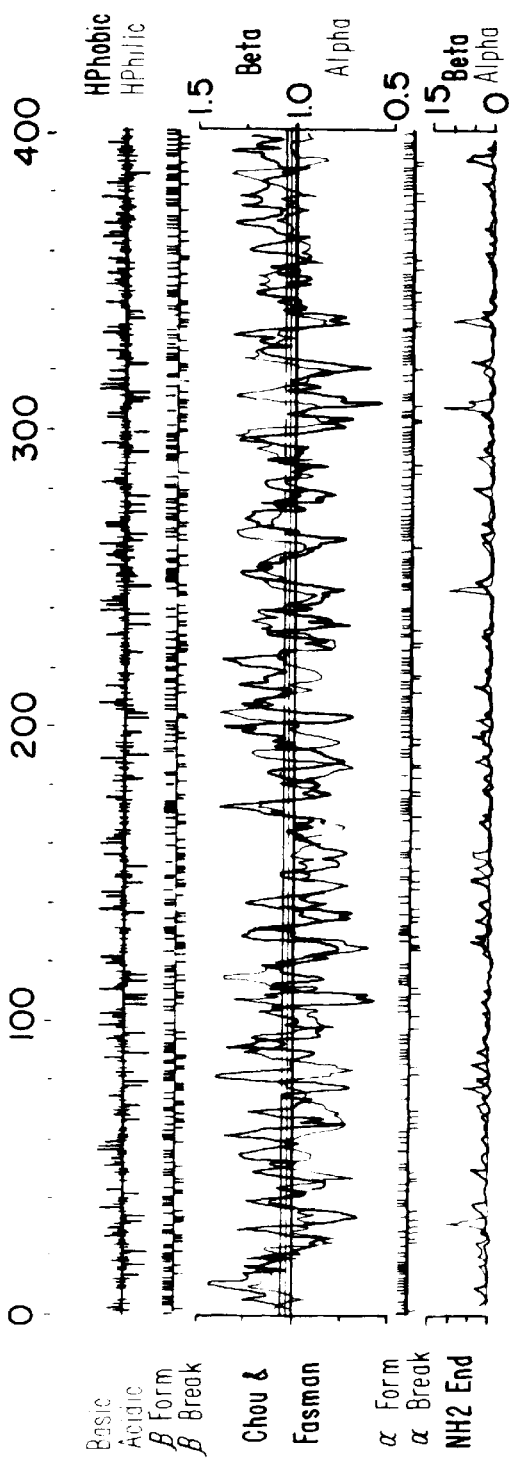

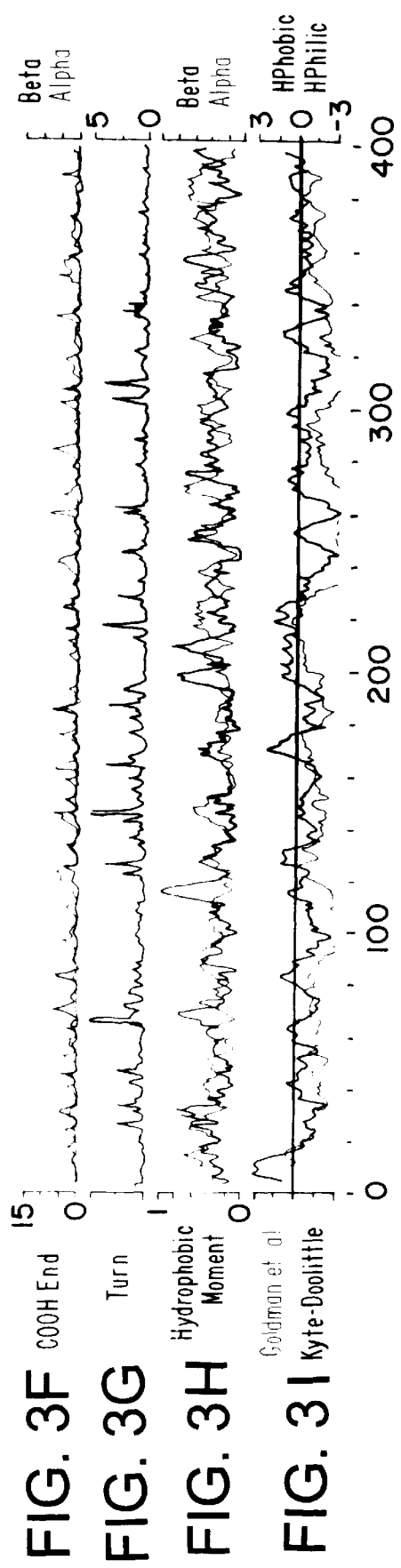

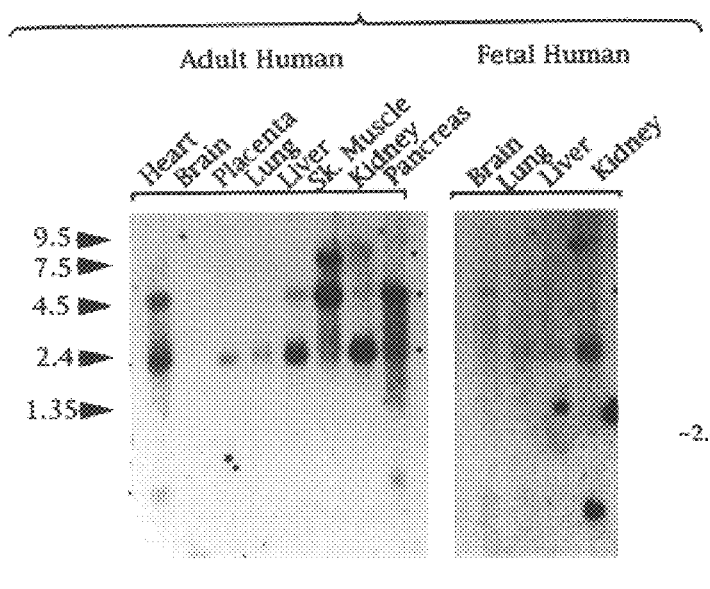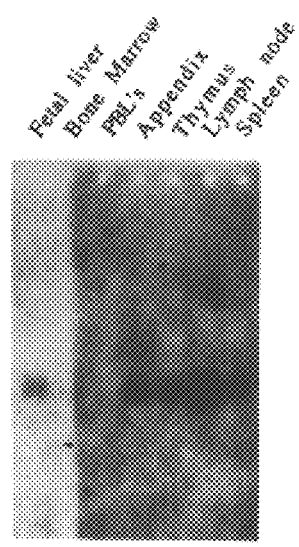

FIG.9A

```
              10                      30                          50
CCTTATATAARACGTCATGATTGCCTGGGCTGCAGAGACGCACCTAGCACTGACCCAGCG
              70                      90                         110
GCTGCCTCCTGAGGTTTCCCGAGGACCACAATGAACAAGTGGCTGTGCTGCGCACTCCTG
                                                  M  N  K  W  L  C  C  A  L  L
             130                     150                         170
GTGCTCCTGGACATCATTGAATGGACAACCCAGGAAACCCTTCCTCCAAAGTACTTGCAT
 V  L  L  D  I  I  E  W  T  T  Q  E  T  L  P  P  K  Y  L  H
             190                     210                         230
TATGACCCAGAAACTGGTCATCAGCTCCTGTGTGACAAATGTGCTCCTGGCACCTACCTA
 Y  D  P  E  T  G  H  Q  L  L  C  D  K  C  A  P  G  T  Y  L
             250                     270                         290
AAACAGCACTGCACAGTGAGGAGGAAGACATTGTGTGTCCCTTGCCCTGACCACTCTTAT
 K  Q  H  C  T  V  R  R  K  T  L  C  V  P  C  P  D  H  S  Y
             310                     330                         350
ACGGACAGCTGGCACACCAGTGATGAGTGTGTGTATTGCAGCCCAGTGTGCAAGGAACTG
 T  D  S  W  H  T  S  D  E  C  V  Y  C  S  P  V  C  K  E  L
             370                     390                         410
CAGTCCGTGAAGCAGGAGTGCAACCGCACCCACAACCGAGTGTGTGAGTGTGAGGAAGGG
 Q  S  V  K  Q  E  C  N  R  T  H  N  R  V  C  E  C  E  E  G
             430                     450                         470
CGTTACCTGGAGATCGAATTCTGCTTGAAGCACCGGAGCTGTCCCCCGGGCTCCGGCGTG
 R  Y  L  E  I  E  F  C  L  K  H  R  S  C  P  P  G  S  G  V
             490                     510                         530
GTGCAAGCTGGAACCCCAGAGCGAAACACAGTTTGCAAAAAATGTCCAGATGGGTTCTTC
 V  Q  A  G  T  P  E  R  N  T  V  C  K  K  C  P  D  G  F  F
             550                     570                         590
TCAGGTGAGACTTCATCGAAAGCACCCTGTATAAAACACACGAACTGCAGCACATTTGGC
 S  G  E  T  S  S  K  A  P  C  I  K  H  T  N  C  S  T  F  G
             610                     630                         650
CTCCTGCTAATTCAGAAAGGAAATGCAACACATGACAACGTGTGTTCCGGAAACAGAGAA
 L  L  L  I  Q  K  G  N  A  T  H  D  N  V  C  S  G  N  R  E
             670                     690                         710
GCCACGCAAAAGTGTGGAATAGATGTCACCCTGTGTGAAGAGGCCTTCTTCAGGTTTGCT
 A  T  Q  K  C  G  I  D  V  T  L  C  E  E  A  F  F  R  F  A
             730                     750                         770
GTTCCTACCAAGATTATACCAAATTGGCTGAGTGTTTTGGTGGACAGTTTGCCTGGGACC
 V  P  T  K  I  I  P  N  W  L  S  V  L  V  D  S  L  P  G  T
```

FIG.9B

```
        790               810                830
AAAGTGAATGCCGAGAGTGTAGAGAGGATAAAACGGAGACACAGCTCACAAGAGCAAACC
 K  V  N  A  E  S  V  E  R  I  K  R  R  H  S  S  Q  E  Q  T
        850               870                890
TTCCAGCTGCTGAAGCTGTGGAAACATCAAAACAGAGACCAGGAAATGGTGAAGAAGATC
 F  Q  L  L  K  L  W  K  H  Q  N  R  D  Q  E  M  V  K  K  I
        910               930                950
ATCCAAGACATTGACCTCTGTGAAAGCAGCGTGCAGCGGCATCTCGGCCACTCGAACCTC
 I  Q  D  I  D  L  C  E  S  S  V  Q  R  H  L  G  H  S  N  L
        970               990               1010
ACCACAGAGCAGCTTCTTGCCTTGATGGAGAGCCTGCCTGGGAAGAAGATCAGCCCAGAA
 T  T  E  Q  L  L  A  L  M  E  S  L  P  G  K  K  I  S  P  E
       1030              1050               1070
GAGATTGAGAGAACGAGAAAGACCTGCAAATCGAGCGAGCAGCTCCTGAAGCTACTCAGT
 E  I  E  R  T  R  K  T  C  K  S  E  Q  L  L  K  L  L  S
       1090              1110               1130
TTATGGAGGATCAAAAATGGTGACCAAGACACCTTGAAGGGCCTGATGTATGCCCTCAAG
 L  W  R  I  K  N  G  D  Q  D  T  L  K  G  L  M  Y  A  L  K
       1150              1170               1190
CACTTGAAAACATCCCACTTTCCCAAAACTGTCACCCACAGTCTGAGGAAGACCATGAGG
 H  L  K  T  S  H  F  P  K  T  V  T  H  S  L  R  K  T  M  R
       1210              1230               1250
TTCCTGCACAGCTTCACAATGTACAGACTGTATCAGAAGCTCTTTTTAGAAATGATAGGG
 F  L  H  S  F  T  M  Y  R  L  Y  Q  K  L  F  L  E  M  I  G
       1270              1290               1310
AATCAGGTTCAATCCGTGAAAATAAGCTGCTTATAACTAGGAATGGTCACTGGGCTGTTT
 N  Q  V  Q  S  V  K  I  S  C  L

CTTCA
```

FIG.9C

```
         10                  30                  50
GTATATATAACGTGATGAGCGTACGGGTGCGGAGACGCACCGGAGCGCTCGCCCAGCCGC
         70                  90                 110
CGYCTCCAAGCCCCTGAGGTTTCCGGGGACCACAATGAACAAGTTGCTGTGCTGCGCGCT
                                         M  N  K  L  L  C  C  A  L
        130                 150                 170
CGTGTTTCTGGACATCTCCATTAAGTGGACCACCCAGGAAACGTTTCCTCCAAAGTACCT
 V  F  L  D  I  S  I  K  W  T  T  Q  E  T  F  P  P  K  Y  L
        190                 210                 230
TCATTATGACGAAGAAACCTCTCATCAGCTGTTGTGTGACAAATGTCCTCCTGGTACCTA
 H  Y  D  E  E  T  S  H  Q  L  L  C  D  K  C  P  P  G  T  Y
        250                 270                 290
CCTAAAACAACACTGTACAGCAAAGTGGAAGACCGTGTGCGCCCCTTGCCCTGACCACTA
 L  K  Q  H  C  T  A  K  W  K  T  V  C  A  P  C  P  D  H  Y
        310                 330                 350
CTACACAGACAGCTGGCACACCAGTGACGAGTGTCTATACTGCAGCCCCGTGTGCAAGGA
 Y  T  D  S  W  H  T  S  D  E  C  L  Y  C  S  P  V  C  K  E
        370                 390                 410
GCTGCAGTACGTCAAGCAGGAGTGCAATCGCACCCACAACCGCGTGTGCGAATGCAAGGA
 L  Q  Y  V  K  Q  E  C  N  R  T  H  N  R  V  C  E  C  K  E
        430                 450                 470
AGGGCGCTACCTTGAGATAGAGTTCTGCTTGAAACATAGGAGCTGCCCTCCTGGATTTGG
 G  R  Y  L  E  I  E  F  C  L  K  H  R  S  C  P  P  G  F  G
        490                 510                 530
AGTGGTGCAAGCTGGAACCCCAGAGCGAAATACAGTTTGCAAAAGATGTCCAGATGGGTT
 V  V  Q  A  G  T  P  E  R  N  T  V  C  K  R  C  P  D  G  F
        550                 570                 590
CTTCTCAAATGAGACGTCATCTAAAGCACCCTGTAGAAAACACACAAATTGCAGTGTCTT
 F  S  N  E  T  S  S  K  A  P  C  R  K  H  T  N  C  S  V  F
        610                 630                 650
TGGTCTCCTGCTAACTCAGAAAGGAAATGCAACACACGACAACATATGTTCCGGAAACAG
 G  L  L  L  T  Q  K  G  N  A  T  H  D  N  I  C  S  G  N  S
        670                 690                 710
TGAATCAACTCAAAAATGTGGAATAGATGTTACCCTGTGTGAGGAGGCATTCTTCAGGTT
 E  S  T  Q  K  C  G  I  D  V  T  L  C  E  E  A  F  F  R  F
        730                 750                 770
TGCTGTTCCTACAAAGTTTACGCCTAACTGGCTTAGTGTCTTGGTAGACAATTTGCCTGG
 A  V  P  T  K  F  T  P  N  W  L  S  V  L  V  D  N  L  P  G
```

FIG. 9D

```
     790                  810                   830
CACCAAAGTAAACGCAGAGAGTGTAGAGAGGATAAAACGGCAACACAGCTCACAAGAACA
 T  K  V  N  A  E  S  V  E  R  I  K  R  Q  H  S  S  Q  E  Q
     850                  870                   890
GACTTTCCAGCTGCTGAAGTTATGGAAACATCAAAACAAAGACCAAGATATAGTCAAGAA
 T  F  Q  L  L  K  L  W  K  H  Q  N  K  D  Q  D  I  V  K  K
     910                  930                   950
GATCATCCAAGATATTGACCTCTGTGAAAACAGCGTGCAGCGGCACATTGGACATGCTAA
 I  I  Q  D  I  D  L  C  E  N  S  V  Q  R  H  I  G  H  A  N
     970                  990                  1010
CCTCACCTTCGAGCAGCTTCGTAGCTTGATGGAAAGCTTACCGGGAAAGAAAGTGGGAGC
 L  T  F  E  Q  L  R  S  L  M  E  S  L  P  G  K  K  V  G  A
    1030                 1050                  1070
AGAAGACATTGAAAAAACAATAAAGGCATGCAAACCCAGTGACCAGATCCTGAAGCTGCT
 E  D  I  E  K  T  I  K  A  C  K  P  S  D  Q  I  L  K  L  L
    1090                 1110                  1130
CAGTTTGTGGCGAATAAAAAATGGCGACCAAGACACCTTGAAGGGCCTAATGCACGCACT
 S  L  W  R  I  K  N  G  D  Q  D  T  L  K  G  L  M  H  A  L
    1150                 1170                  1190
AAAGCACTCAAAGACGTACCACTTTCCCAAAACTGTCACTCAGAGTCTAAAGAAGACCAT
 K  H  S  K  T  Y  H  F  P  K  T  V  T  Q  S  L  K  K  T  I
    1210                 1230                  1250
CAGGTTCCTTCACAGCTTCACAATGTACAAATTGTATCAGAAGTTATTTTTAGAAATGAT
 R  F  L  H  S  F  T  M  Y  K  L  Y  Q  K  L  F  L  E  M  I
    1270                 1290                  1310
AGGTAACCAGGTCCAATCAGTAAAAATAAGCTGCTTATAACTGGAAATGGCCATTGAGCT
 G  N  Q  V  Q  S  V  K  I  S  C  L
    1330                 1350
GTTTCCTCACAATTGGCGAGATCCCATGGATGATAA
```

FIG.9E

```
muosteo.frg   MNKWLCCALLVLLDIHEWTFTQQETFPPKYLHYDPETGHQLLCDKCAPGTYL  50
ratosteo.frg  MNKWLCCALLVLVFLDIHEWTFTQQETFPPKYLHYDPETGRQLLCDKCAPGTYL  50
huosteo.frg   MNKLLCCALVFLDISIKWTFTQETFPPKYLHYDETSHQLLCDKCPPGTYL  50 muosteo.frg   KQHCTVRRKKTLCVPCPDHSYTDSWHTSDECVYCSPVCKELQSVKQECNRT  100
ratosteo.frg  KQHCTVRRKKTLCVPCPDDYSYTDSWHTSDECVYCSPVCKELQTVKQECNRT  100
huosteo.frg   KQHCTAKWKIVCAPCPDDYYTDSWHTSDECLYCSPVCKELQYVKQECNRT  100 muosteo.frg   HNRVCECEEEGRYLEIEFCLKHRSCPPGSGVVQAGTPERNTVCKKCPDGFF  150
ratosteo.frg  HNRVCECEEEGRYLEIELFCLKHRSCPPGLGVVQAGTPERNTVCKRCPDGFF  150
huosteo.frg   HNRVCECKEGRYLEIEFCLKHRSCPPGFGVVQAGTPERNTVCKRCPDGFF  150 muosteo.frg   SGETSSKAPCLIKHTNCSTFGLLLIQKGNATHDNVCSGNREATQKCGIDVT  200
ratosteo.frg  SGETSSKAPCLIKHTNCSSIGLLLIQKGNATHDNVCSGNREATQNCGIDVT  200
huosteo.frg   SNETSSKAPCRKHTNCSVFGLLLTQKGNATHDNICSGNSESTQKCGIDVT  200
```

FIG.9F

```
                                                                                              250
muosteo.frg  LCEEAFFRFAVPTKIHPNWLSVLVDSLPGTKVNAESVERIKRRHSSQET     250
ratosteo.frg LCEEAFFRFAVPTKIHPNWLSVLVDSLPGTKVNAESVERIKRRHSSQET     250
huosteo.frg  LCEEAFFRFAVPFKFTPNWLSVLVDNLPGTKVNAESVERIKRQHSSQEQ 300
muosteo.frg  FQLLKLWKKHQNRDQEMVKKIIQDIDLCESSVQRHLGHSNLTTEQLLALME   300
ratosteo.frg FQLLKLWKKHQNRDQEMVKKIIQDIDLCESSVQRHIGHANLTTEQLRHLME   300
huosteo.frg  FQLLKLWKHQNKDQDIVKKIIQDIDLCENSVQRHIGHANLTFEQLRSLME 350
muosteo.frg  SLPGKKKISPEEIERTRKTCKSSEQLLKLLSLWRIKNGDQDTLKGLMYALK   350
ratosteo.frg SLPGKKKISPEEIERTRKTCKPSEQLLKLLSLWRIKNGDQDTLKGLMYALK   350
huosteo.frg  SLPGKKVGAEDIEKTIKACKPSDQILKLLSLWRIKNGDQDTLKGLMHALK 400
muosteo.frg  HLKTSHFPKTVTHSLRKKTMRFLHSFTMYRLYQKLFLEMIGNQVQSVKISC   400
ratosteo.frg HLKAYHFPKTVTHSLRKKTIRFLHSFTMYRLYQKLFLEMIGNQVQSVKISC   400
huosteo.frg  HSKTYHFPKTVTQSLKKTIRFLHSFTMYKLYQKLFLEMIGNQVQSVKISC 401
muosteo.frg  L   401
ratosteo.frg L   401
huosteo.frg  L
```

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
       (A) LENGTH: 2432 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 124..1326

(xi) SEQUENCE DESCRIPTION: SEQ ID NO:1:

```
ATCAAAGGCA GGGCATACTT CCTGTTGCCC AGACCTTATA TAAAACGTCA TGTTCGCCTG        60

GGCAGCAGAG AAGCACCTAG CACTGGCCCA GCGGCTGCCG CCTGAGGTTT CCAGAGGACC       120

ACA ATG AAC AAG TGG CTG TGC TGT GCA CTC CTG GTG TTC TTG GAC ATC        168
    Met Asn Lys Trp Leu Cys Cys Ala Leu Leu Val Phe Leu Asp Ile
    1               5                  10                  15

ATT GAA TGG ACA ACC CAG GAA ACC TTT CCT CCA AAA TAC TTG CAT TAT        216
Ile Glu Trp Thr Thr Gln Glu Thr Phe Pro Pro Lys Tyr Leu His Tyr
                20                  25                  30

GAC CCA GAA ACC GGA CGT CAG CTC TTG TGT GAC AAA TGT GCT CCT GGC        264
Asp Pro Glu Thr Gly Arg Gln Leu Leu Cys Asp Lys Cys Ala Pro Gly
            35                  40                  45

ACC TAC CTA AAA CAG CAC TGC ACA GTC AGG AGG AAG ACA CTG TGT GTC        312
Thr Tyr Leu Lys Gln His Cys Thr Val Arg Arg Lys Thr Leu Cys Val
        50                  55                  60

CCT TGC CCT GAC TAC TCT TAT ACA GAC AGC TGG CAC ACG AGT GAT GAA        360
Pro Cys Pro Asp Tyr Ser Tyr Thr Asp Ser Trp His Thr Ser Asp Glu
    65                  70                  75

TGC GTG TAC TGC AGC CCC GTG TGC AAG GAA CTG CAG ACC GTG AAA CAG        408
Cys Val Tyr Cys Ser Pro Val Cys Lys Glu Leu Gln Thr Val Lys Gln
80                  85                  90                  95

GAG TGC AAC CGC ACC CAC AAC CGA GTG TGC GAA TGT GAG GAA GGG CGC        456
Glu Cys Asn Arg Thr His Asn Arg Val Cys Glu Cys Glu Glu Gly Arg
                100                 105                 110

TAC CTG GAG CTC GAA TTC TGC TTG AAG CAC CGG AGC TGT CCC CCA GGC        504
Tyr Leu Glu Leu Glu Phe Cys Leu Lys His Arg Ser Cys Pro Pro Gly
            115                 120                 125

TTG GGT GTG CTG CAG GCT GGG ACC CCA GAG CGA AAC ACG GTT TGC AAA        552
Leu Gly Val Leu Gln Ala Gly Thr Pro Glu Arg Asn Thr Val Cys Lys
        130                 135                 140

AGA TGT CCG GAT GGG TTC TTC TCA GGT GAG ACG TCA TCG AAA GCA CCC        600
Arg Cys Pro Asp Gly Phe Phe Ser Gly Glu Thr Ser Ser Lys Ala Pro
145                 150                 155

TGT AGG AAA CAC ACC AAC TGC AGC TCA CTT GGC CTC CTG CTA ATT CAG        648
Cys Arg Lys His Thr Asn Cys Ser Ser Leu Gly Leu Leu Leu Ile Gln
160                 165                 170                 175

AAA GGA AAT GCA ACA CAT GAC AAT GTA TGT TCC GGA AAC AGA GAA GCA        696
Lys Gly Asn Ala Thr His Asp Asn Val Cys Ser Gly Asn Arg Glu Ala
                180                 185                 190

ACT CAA AAT TGT GGA ATA GAT GTC ACC CTG TGC GAA GAG GCA TTC TTC        744
Thr Gln Asn Cys Gly Ile Asp Val Thr Leu Cys Glu Glu Ala Phe Phe
            195                 200                 205
```

```
AGG TTT GCT GTG CCT ACC AAG ATT ATA CCG AAT TGG CTG AGT GTT CTG        792
Arg Phe Ala Val Pro Thr Lys Ile Ile Pro Asn Trp Leu Ser Val Leu
        210             215             220

GTG GAC AGT TTG CCT GGG ACC AAA GTG AAT GCA GAG AGT GTA GAG AGG        840
Val Asp Ser Leu Pro Gly Thr Lys Val Asn Ala Glu Ser Val Glu Arg
        225             230             235

ATA AAA CGG AGA CAC AGC TCG CAA GAG CAA ACT TTC CAG CTA CTT AAG        888
Ile Lys Arg Arg His Ser Ser Gln Glu Gln Thr Phe Gln Leu Leu Lys
240             245             250             255

CTG TGG AAG CAT CAA AAC AGA GAC CAG GAA ATG GTG AAG AAG ATC ATC        936
Leu Trp Lys His Gln Asn Arg Asp Gln Glu Met Val Lys Lys Ile Ile
                260             265             270

CAA GAC ATT GAC CTC TGT GAA AGC AGT GTG CAA CGG CAT ATC GGC CAC        984
Gln Asp Ile Asp Leu Cys Glu Ser Ser Val Gln Arg His Ile Gly His
            275             280             285

GCG AAC CTC ACC ACA GAG CAG CTC CGC ATC TTG ATG GAG AGC TTG CCT       1032
Ala Asn Leu Thr Thr Glu Gln Leu Arg Ile Leu Met Glu Ser Leu Pro
        290             295             300

GGG AAG AAG ATC AGC CCA GAC GAG ATT GAG AGA ACG AGA AAG ACC TGC       1080
Gly Lys Lys Ile Ser Pro Asp Glu Ile Glu Arg Thr Arg Lys Thr Cys
305             310             315

AAA CCC AGC GAG CAG CTC CTG AAG CTA CTG AGC TTG TGG AGG ATC AAA       1128
Lys Pro Ser Glu Gln Leu Leu Lys Leu Leu Ser Leu Trp Arg Ile Lys
320             325             330             335

AAT GGA GAC CAA GAC ACC TTG AAG GGC CTG ATG TAC GCA CTC AAG CAC       1176
Asn Gly Asp Gln Asp Thr Leu Lys Gly Leu Met Tyr Ala Leu Lys His
                340             345             350

TTG AAA GCA TAC CAC TTT CCC AAA ACC GTC ACC CAC AGT CTG AGG AAG       1224
Leu Lys Ala Tyr His Phe Pro Lys Thr Val Thr His Ser Leu Arg Lys
            355             360             365

ACC ATC AGG TTC TTG CAC AGC TTC ACC ATG TAC CGA TTG TAT CAG AAA       1272
Thr Ile Arg Phe Leu His Ser Phe Thr Met Tyr Arg Leu Tyr Gln Lys
        370             375             380

CTC TTT CTA GAA ATG ATA GGG AAT CAG GTT CAA TCA GTG AAG ATA AGC       1320
Leu Phe Leu Glu Met Ile Gly Asn Gln Val Gln Ser Val Lys Ile Ser
385             390             395

TGC TTA TAGTTAGGAA TGGTCACTGG GCTGTTTCTT CAGGATGGGC CAACACTGAT        1376
Cys Leu
400

GGAGCAGATG GCTGCTTCTC CGGCTCTTGA AATGGCAGTT GATTCCTTTC TCATCAGTTG     1436

GTGGGAATGA AGATCCTCCA GCCCAACACA CACACTGGGG AGTCTGAGTC AGGAGAGTGA     1496

GGCAGGCTAT TTGATAATTG TGCAAAGCTG CCAGGTGTAC ACCTAGAAAG TCAAGCACCC     1556

TGAGAAAGAG GATATTTTTA TAACCTCAAA CATAGGCCCT TTCCTTCCTC TCCTTATGGA     1616

TGAGTACTCA GAAGGCTTCT ACTATCTTCT GTGTCATCCC TAGATGAAGG CCTCTTTTAT     1676

TTATTTTTTT ATTCTTTTTT TCGGAGCTGG GGACCGAACC CAGGGCCTTG CGCTTGCGAG     1736

GCAAGTGCTC TACCACTGAG CTAAATCTCC AACCCCTGAA GGCCTCTTTC TTTCTGCCTC     1796

TGATAGTCTA TGACATTCTT TTTTCTACAA TTCGTATCGG GTGCACGAGC CTTATCCCAT     1856

TTGTAGGTTT CTAGGCAAGT TGACCGTTAG CTATTTTTCC CTCTGAAGAT TGATTCGAG      1916

TTGCAGACTT GGCTAGACAA GCAGGGGTAG GTTATGGTAG TTTATTTAAC AGACTGCCAC     1976

CAGGAGTCCA GTGTTTCTTG TTCCTCTGTA GTTGTACCTA AGCTGACTCC AAGTACATTT     2036

AGTATGAAAA ATAATCAACA AATTTTATTC CTTCTATCAA CATTGGCTAG CTTTGTTTCA     2096

GGGCACTAAA AGAAACTACT ATATGGAGAA AGAATTGATA TTGCCCCCAA CGTTCAACAA     2156
```

```
CCCAATAGTT TATCCAGCTG TCATGCCTGG TTCAGTGTCT ACTGACTATG CGCCCTCTTA      2216

TTACTGCATG CAGTAATTCA ACTGGAAATA GTAATAATAA TAATAGAAAT AAAATCTAGA      2276

CTCCATTGGA TCTCTCTGAA TATGGGAATA TCTAACTTAA GAAGCTTTGA GATTTCAGTT      2336

GTGTTAAAGG CTTTTATTAA AAAGCTGATG CTCTTCTGTA AAAGTTACTA ATATATCTGT      2396

AAGACTATTA CAGTATTGCT ATTTATATCC ATCCAG                                2432
```

(2) INFORMATION FOR SEQ ID NO:2:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Lys Trp Leu Cys Cys Ala Leu Leu Val Phe Leu Asp Ile Ile
 1               5                  10                  15

Glu Trp Thr Thr Gln Glu Thr Phe Pro Pro Lys Tyr Leu His Tyr Asp
             20                  25                  30

Pro Glu Thr Gly Arg Gln Leu Leu Cys Asp Lys Cys Ala Pro Gly Thr
         35                  40                  45

Tyr Leu Lys Gln His Cys Thr Val Arg Arg Lys Thr Leu Cys Val Pro
     50                  55                  60

Cys Pro Asp Tyr Ser Tyr Thr Asp Ser Trp His Thr Ser Asp Glu Cys
 65                  70                  75                  80

Val Tyr Cys Ser Pro Val Cys Lys Glu Leu Gln Thr Val Lys Gln Glu
                 85                  90                  95

Cys Asn Arg Thr His Asn Arg Val Cys Glu Cys Glu Glu Gly Arg Tyr
            100                 105                 110

Leu Glu Leu Glu Phe Cys Leu Lys His Arg Ser Cys Pro Pro Gly Leu
        115                 120                 125

Gly Val Leu Gln Ala Gly Thr Pro Glu Arg Asn Thr Val Cys Lys Arg
    130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Asn Cys Gly Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
    210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Ile Gly His Ala
        275                 280                 285

Asn Leu Thr Thr Glu Gln Leu Arg Ile Leu Met Glu Ser Leu Pro Gly
    290                 295                 300
```

```
Lys Lys Ile Ser Pro Asp Glu Ile Glu Arg Thr Arg Lys Thr Cys Lys
305                 310                 315                 320

Pro Ser Glu Gln Leu Leu Lys Leu Leu Ser Leu Trp Arg Ile Lys Asn
            325                 330                 335

Gly Asp Gln Asp Thr Leu Lys Gly Leu Met Tyr Ala Leu Lys His Leu
            340                 345                 350

Lys Ala Tyr His Phe Pro Lys Thr Val Thr His Ser Leu Arg Lys Thr
            355                 360                 365

Ile Arg Phe Leu His Ser Phe Thr Met Tyr Arg Leu Tyr Gln Lys Leu
370                 375                 380

Phe Leu Glu Met Ile Gly Asn Gln Val Gln Ser Val Lys Ile Ser Cys
385                 390                 395                 400

Leu
```

(2) INFORMATION FOR SEQ ID NO:3:

(i) SEQUENCE CHARACTERISTICS:
        (A) LENGTH: 1324 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 90..1292

(xi) SEQUENCE DESCRIPTION: SEQ ID NO:3:

```
CCTTATATAA ACGTCATGAT TGCCTGGGCT GCAGAGACGC ACCTAGCACT GACCCAGCGG      60

CTGCCTCCTG AGGTTTCCCG AGGACCACA ATG AAC AAG TGG CTG TGC TGC GCA      113
                               Met Asn Lys Trp Leu Cys Cys Ala
                                 1               5

CTC CTG GTG CTC CTG GAC ATC ATT GAA TGG ACA ACC CAG GAA ACC CTT      161
Leu Leu Val Leu Leu Asp Ile Ile Glu Trp Thr Thr Gln Glu Thr Leu
     10                  15                  20

CCT CCA AAG TAC TTG CAT TAT GAC CCA GAA ACT GGT CAT CAG CTC CTG      209
Pro Pro Lys Tyr Leu His Tyr Asp Pro Glu Thr Gly His Gln Leu Leu
 25                  30                  35                  40

TGT GAC AAA TGT GCT CCT GGC ACC TAC CTA AAA CAG CAC TGC ACA GTG      257
Cys Asp Lys Cys Ala Pro Gly Thr Tyr Leu Lys Gln His Cys Thr Val
             45                  50                  55

AGG AGG AAG ACA TTG TGT GTC CCT TGC CCT GAC CAC TCT TAT ACG GAC      305
Arg Arg Lys Thr Leu Cys Val Pro Cys Pro Asp His Ser Tyr Thr Asp
             60                  65                  70

AGC TGG CAC ACC AGT GAT GAG TGT GTG TAT TGC AGC CCA GTG TGC AAG      353
Ser Trp His Thr Ser Asp Glu Cys Val Tyr Cys Ser Pro Val Cys Lys
             75                  80                  85

GAA CTG CAG TCC GTG AAG CAG GAG TGC AAC CGC ACC CAC AAC CGA GTG      401
Glu Leu Gln Ser Val Lys Gln Glu Cys Asn Arg Thr His Asn Arg Val
         90                  95                 100

TGT GAG TGT GAG GAA GGG CGT TAC CTG GAG ATC GAA TTC TGC TTG AAG      449
Cys Glu Cys Glu Glu Gly Arg Tyr Leu Glu Ile Glu Phe Cys Leu Lys
105                 110                 115                 120

CAC CGG AGC TGT CCC CCG GGC TCC GGC GTG GTG CAA GCT GGA ACC CCA      497
His Arg Ser Cys Pro Pro Gly Ser Gly Val Val Gln Ala Gly Thr Pro
                125                 130                 135

GAG CGA AAC ACA GTT TGC AAA AAA TGT CCA GAT GGG TTC TTC TCA GGT      545
Glu Arg Asn Thr Val Cys Lys Lys Cys Pro Asp Gly Phe Phe Ser Gly
            140                 145                 150
```

```
GAG ACT TCA TCG AAA GCA CCC TGT ATA AAA CAC ACG AAC TGC AGC ACA        593
Glu Thr Ser Ser Lys Ala Pro Cys Ile Lys His Thr Asn Cys Ser Thr
        155                 160                 165

TTT GGC CTC CTG CTA ATT CAG AAA GGA AAT GCA ACA CAT GAC AAC GTG        641
Phe Gly Leu Leu Leu Ile Gln Lys Gly Asn Ala Thr His Asp Asn Val
170                 175                 180

TGT TCC GGA AAC AGA GAA GCC ACG CAA AAG TGT GGA ATA GAT GTC ACC        689
Cys Ser Gly Asn Arg Glu Ala Thr Gln Lys Cys Gly Ile Asp Val Thr
185                 190                 195                 200

CTG TGT GAA GAG GCC TTC TTC AGG TTT GCT GTT CCT ACC AAG ATT ATA        737
Leu Cys Glu Glu Ala Phe Phe Arg Phe Ala Val Pro Thr Lys Ile Ile
                205                 210                 215

CCA AAT TGG CTG AGT GTT TTG GTG GAC AGT TTG CCT GGG ACC AAA GTG        785
Pro Asn Trp Leu Ser Val Leu Val Asp Ser Leu Pro Gly Thr Lys Val
                220                 225                 230

AAT GCC GAG AGT GTA GAG AGG ATA AAA CGG AGA CAC AGC TCA CAA GAG        833
Asn Ala Glu Ser Val Glu Arg Ile Lys Arg Arg His Ser Ser Gln Glu
        235                 240                 245

CAA ACC TTC CAG CTG CTG AAG CTG TGG AAA CAT CAA AAC AGA GAC CAG        881
Gln Thr Phe Gln Leu Leu Lys Leu Trp Lys His Gln Asn Arg Asp Gln
        250                 255                 260

GAA ATG GTG AAG AAG ATC ATC CAA GAC ATT GAC CTC TGT GAA AGC AGC        929
Glu Met Val Lys Lys Ile Ile Gln Asp Ile Asp Leu Cys Glu Ser Ser
265                 270                 275                 280

GTG CAG CGG CAT CTC GGC CAC TCG AAC CTC ACC ACA GAG CAG CTT CTT        977
Val Gln Arg His Leu Gly His Ser Asn Leu Thr Thr Glu Gln Leu Leu
                285                 290                 295

GCC TTG ATG GAG AGC CTG CCT GGG AAG AAG ATC AGC CCA GAA GAG ATT       1025
Ala Leu Met Glu Ser Leu Pro Gly Lys Lys Ile Ser Pro Glu Glu Ile
                300                 305                 310

GAG AGA ACG AGA AAG ACC TGC AAA TCG AGC GAG CAG CTC CTG AAG CTA       1073
Glu Arg Thr Arg Lys Thr Cys Lys Ser Ser Glu Gln Leu Leu Lys Leu
        315                 320                 325

CTC AGT TTA TGG AGG ATC AAA AAT GGT GAC CAA GAC ACC TTG AAG GGC       1121
Leu Ser Leu Trp Arg Ile Lys Asn Gly Asp Gln Asp Thr Leu Lys Gly
330                 335                 340

CTG ATG TAT GCC CTC AAG CAC TTG AAA ACA TCC CAC TTT CCC AAA ACT       1169
Leu Met Tyr Ala Leu Lys His Leu Lys Thr Ser His Phe Pro Lys Thr
345                 350                 355                 360

GTC ACC CAC AGT CTG AGG AAG ACC ATG AGG TTC CTG CAC AGC TTC ACA       1217
Val Thr His Ser Leu Arg Lys Thr Met Arg Phe Leu His Ser Phe Thr
                365                 370                 375

ATG TAC AGA CTG TAT CAG AAG CTC TTT TTA GAA ATG ATA GGG AAT CAG       1265
Met Tyr Arg Leu Tyr Gln Lys Leu Phe Leu Glu Met Ile Gly Asn Gln
        380                 385                 390

GTT CAA TCC GTG AAA ATA AGC TGC TTA TAACTAGGAA TGGTCACTGG             1312
Val Gln Ser Val Lys Ile Ser Cys Leu
        395                 400

GCTGTTTCTT CA                                                        1324
```

(2) INFORMATION FOR SEQ ID NO:4:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Lys Trp Leu Cys Cys Ala Leu Leu Val Leu Leu Asp Ile Ile

-continued

```
  1               5                   10                  15
Glu Trp Thr Thr Gln Glu Thr Leu Pro Pro Lys Tyr Leu His Tyr Asp
            20                  25                  30

Pro Glu Thr Gly His Gln Leu Leu Cys Asp Lys Cys Ala Pro Gly Thr
            35                  40                  45

Tyr Leu Lys Gln His Cys Thr Val Arg Arg Lys Thr Leu Cys Val Pro
            50                  55                  60

Cys Pro Asp His Ser Tyr Thr Asp Ser Trp His Thr Ser Asp Glu Cys
 65                      70                  75                  80

Val Tyr Cys Ser Pro Val Cys Lys Glu Leu Gln Ser Val Lys Gln Glu
                85                  90                  95

Cys Asn Arg Thr His Asn Arg Val Cys Glu Cys Glu Glu Gly Arg Tyr
            100                 105                 110

Leu Glu Ile Glu Phe Cys Leu Lys His Arg Ser Cys Pro Pro Gly Ser
            115                 120                 125

Gly Val Val Gln Ala Gly Thr Pro Glu Arg Asn Thr Val Cys Lys Lys
            130                 135                 140

Cys Pro Asp Gly Phe Phe Ser Gly Glu Thr Ser Ser Lys Ala Pro Cys
145                 150                 155                 160

Ile Lys His Thr Asn Cys Ser Thr Phe Gly Leu Leu Leu Ile Gln Lys
            165                 170                 175

Gly Asn Ala Thr His Asp Asn Val Cys Ser Gly Asn Arg Glu Ala Thr
            180                 185                 190

Gln Lys Cys Gly Ile Asp Val Thr Leu Cys Glu Glu Ala Phe Phe Arg
            195                 200                 205

Phe Ala Val Pro Thr Lys Ile Ile Pro Asn Trp Leu Ser Val Leu Val
            210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
            245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Leu Gly His Ser
            275                 280                 285

Asn Leu Thr Thr Glu Gln Leu Leu Ala Leu Met Glu Ser Leu Pro Gly
            290                 295                 300

Lys Lys Ile Ser Pro Glu Glu Ile Glu Arg Thr Arg Lys Thr Cys Lys
305                 310                 315                 320

Ser Ser Glu Gln Leu Leu Lys Leu Leu Ser Leu Trp Arg Ile Lys Asn
            325                 330                 335

Gly Asp Gln Asp Thr Leu Lys Gly Leu Met Tyr Ala Leu Lys His Leu
            340                 345                 350

Lys Thr Ser His Phe Pro Lys Thr Val Thr His Ser Leu Arg Lys Thr
            355                 360                 365

Met Arg Phe Leu His Ser Phe Thr Met Tyr Arg Leu Tyr Gln Lys Leu
            370                 375                 380

Phe Leu Glu Met Ile Gly Asn Gln Val Gln Ser Val Lys Ile Ser Cys
385                 390                 395                 400

Leu
```

(2) INFORMATION FOR SEQ ID NO:5:

(i) SEQUENCE CHARACTERISTICS:
    (A) LENGTH: 1355 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 94..1296

(xi) SEQUENCE DESCRIPTION: SEQ ID NO:5:

```
GTATATATAA CGTGATGAGC GTACGGGTGC GGAGACGCAC CGGAGCGCTC GCCCAGCCGC        60

CGCTCCAAGC CCCTGAGGTT TCCGGGGACC ACA ATG AAC AAG TTG CTG TGC TGC       114
                                    Met Asn Lys Leu Leu Cys Cys
                                     1               5

GCG CTC GTG TTT CTG GAC ATC TCC ATT AAG TGG ACC ACC CAG GAA ACG        162
Ala Leu Val Phe Leu Asp Ile Ser Ile Lys Trp Thr Thr Gln Glu Thr
         10                  15                  20

TTT CCT CCA AAG TAC CTT CAT TAT GAC GAA GAA ACC TCT CAT CAG CTG        210
Phe Pro Pro Lys Tyr Leu His Tyr Asp Glu Glu Thr Ser His Gln Leu
 25                  30                  35

TTG TGT GAC AAA TGT CCT CCT GGT ACC TAC CTA AAA CAA CAC TGT ACA        258
Leu Cys Asp Lys Cys Pro Pro Gly Thr Tyr Leu Lys Gln His Cys Thr
 40                  45                  50                  55

GCA AAG TGG AAG ACC GTG TGC GCC CCT TGC CCT GAC CAC TAC TAC ACA        306
Ala Lys Trp Lys Thr Val Cys Ala Pro Cys Pro Asp His Tyr Tyr Thr
             60                  65                  70

GAC AGC TGG CAC ACC AGT GAC GAG TGT CTA TAC TGC AGC CCC GTG TGC        354
Asp Ser Trp His Thr Ser Asp Glu Cys Leu Tyr Cys Ser Pro Val Cys
         75                  80                  85

AAG GAG CTG CAG TAC GTC AAG CAG GAG TGC AAT CGC ACC CAC AAC CGC        402
Lys Glu Leu Gln Tyr Val Lys Gln Glu Cys Asn Arg Thr His Asn Arg
     90                  95                 100

GTG TGC GAA TGC AAG GAA GGG CGC TAC CTT GAG ATA GAG TTC TGC TTG        450
Val Cys Glu Cys Lys Glu Gly Arg Tyr Leu Glu Ile Glu Phe Cys Leu
105                 110                 115

AAA CAT AGG AGC TGC CCT CCT GGA TTT GGA GTG GTG CAA GCT GGA ACC        498
Lys His Arg Ser Cys Pro Pro Gly Phe Gly Val Val Gln Ala Gly Thr
120                 125                 130                 135

CCA GAG CGA AAT ACA GTT TGC AAA AGA TGT CCA GAT GGG TTC TTC TCA        546
Pro Glu Arg Asn Thr Val Cys Lys Arg Cys Pro Asp Gly Phe Phe Ser
                140                 145                 150

AAT GAG ACG TCA TCT AAA GCA CCC TGT AGA AAA CAC ACA AAT TGC AGT        594
Asn Glu Thr Ser Ser Lys Ala Pro Cys Arg Lys His Thr Asn Cys Ser
             155                 160                 165

GTC TTT GGT CTC CTG CTA ACT CAG AAA GGA AAT GCA ACA CAC GAC AAC        642
Val Phe Gly Leu Leu Leu Thr Gln Lys Gly Asn Ala Thr His Asp Asn
         170                 175                 180

ATA TGT TCC GGA AAC AGT GAA TCA ACT CAA AAA TGT GGA ATA GAT GTT        690
Ile Cys Ser Gly Asn Ser Glu Ser Thr Gln Lys Cys Gly Ile Asp Val
     185                 190                 195

ACC CTG TGT GAG GAG GCA TTC TTC AGG TTT GCT GTT CCT ACA AAG TTT        738
Thr Leu Cys Glu Glu Ala Phe Phe Arg Phe Ala Val Pro Thr Lys Phe
200                 205                 210                 215

ACG CCT AAC TGG CTT AGT GTC TTG GTA GAC AAT TTG CCT GGC ACC AAA        786
Thr Pro Asn Trp Leu Ser Val Leu Val Asp Asn Leu Pro Gly Thr Lys
                220                 225                 230

GTA AAC GCA GAG AGT GTA GAG AGG ATA AAA CGG CAA CAC AGC TCA CAA        834
Val Asn Ala Glu Ser Val Glu Arg Ile Lys Arg Gln His Ser Ser Gln
             235                 240                 245
```

```
GAA CAG ACT TTC CAG CTG CTG AAG TTA TGG AAA CAT CAA AAC AAA GCC    882
Glu Gln Thr Phe Gln Leu Leu Lys Leu Trp Lys His Gln Asn Lys Ala
            250                 255                 260

CAA GAT ATA GTC AAG AAG ATC ATC CAA GAT ATT GAC CTC TGT GAA AAC    930
Gln Asp Ile Val Lys Lys Ile Ile Gln Asp Ile Asp Leu Cys Glu Asn
        265                 270                 275

AGC GTG CAG CGG CAC ATT GGA CAT GCT AAC CTC ACC TTC GAG CAG CTT    978
Ser Val Gln Arg His Ile Gly His Ala Asn Leu Thr Phe Glu Gln Leu
280                 285                 290                 295

CGT AGC TTG ATG GAA AGC TTA CCG GGA AAG AAA GTG GGA GCA GAA GAC   1026
Arg Ser Leu Met Glu Ser Leu Pro Gly Lys Lys Val Gly Ala Glu Asp
                300                 305                 310

ATT GAA AAA ACA ATA AAG GCA TGC AAA CCC AGT GAC CAG ATC CTG AAG   1074
Ile Glu Lys Thr Ile Lys Ala Cys Lys Pro Ser Asp Gln Ile Leu Lys
            315                 320                 325

CTG CTC AGT TTG TGG CGA ATA AAA AAT GGC GAC CAA GAC ACC TTG AAG   1122
Leu Leu Ser Leu Trp Arg Ile Lys Asn Gly Asp Gln Asp Thr Leu Lys
        330                 335                 340

GGC CTA ATG CAC GCA CTA AAG CAC TCA AAG ACG TAC CAC TTT CCC AAA   1170
Gly Leu Met His Ala Leu Lys His Ser Lys Thr Tyr His Phe Pro Lys
345                 350                 355

ACT GTC ACT CAG AGT CTA AAG AAG ACC ATC AGG TTC CTT CAC AGC TTC   1218
Thr Val Thr Gln Ser Leu Lys Lys Thr Ile Arg Phe Leu His Ser Phe
360                 365                 370                 375

ACA ATG TAC AAA TTG TAT CAG AAG TTA TTT TTA GAA ATG ATA GGT AAC   1266
Thr Met Tyr Lys Leu Tyr Gln Lys Leu Phe Leu Glu Met Ile Gly Asn
                380                 385                 390

CAG GTC CAA TCA GTA AAA ATA AGC TGC TTA TAACTGGAAA TGGCCATTGA     1316
Gln Val Gln Ser Val Lys Ile Ser Cys Leu
            395                 400

GCTGTTTCCT CACAATTGGC GAGATCCCAT GGATGATAA                        1355

(2) INFORMATION FOR SEQ ID NO:6:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Lys Leu Leu Cys Cys Ala Leu Val Phe Leu Asp Ile Ser Ile
 1               5                  10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125
```

```
Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Lys Ile Ile Gln
                260                 265                 270

Asp Ile Asp Leu Cys Glu Asn Ser Val Gln Arg His Ile Gly His Ala
            275                 280                 285

Asn Leu Thr Phe Glu Gln Leu Arg Ser Leu Met Glu Ser Leu Pro Gly
        290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
                340                 345                 350

Lys Thr Tyr His Phe Pro Lys Thr Val Thr Gln Ser Leu Lys Lys Thr
                355                 360                 365

Ile Arg Phe Leu His Ser Phe Thr Met Tyr Lys Leu Tyr Gln Lys Leu
            370                 375                 380

Phe Leu Glu Met Ile Gly Asn Gln Val Gln Ser Val Lys Ile Ser Cys
385                 390                 395                 400

Leu (2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:7:

AAAGGAAGGA AAAAAGCGGC CGCTACANNN NNNNNT                                  36

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA
```

```
    (xi) SEQUENCE DESCRIPTION: SEQ ID NO:8:

TCGACCCACG CGTCCG                                                  16

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGGACGCGTG GG                                                      12

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TGTAAAACGA CGGCCAGT                                                18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAGGAAACAG CTATGACC                                                18

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CAATTAACCC TCACTAAAGG                                              20

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCATTATGAC CCAGAAACCG GAC                                          23
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AGGTAGCGCC CTTCCTCACA TTC        23

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GACTAGTCCC ACAATGAACA AGTGGCTGTG        30

(2) INFORMATION FOR SEQ ID NO:16:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

ATAAGAATGC GGCCGCTAAA CTATGAAACA GCCCAGTGAC CATTC        45

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCCTCTAGAA AGAGCTGGGA C        21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CGCCGTGTTC CATTTATGAG C        21

(2) INFORMATION FOR SEQ ID NO:19:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

ATCAAAGGCA GGGCATACTT CCTG                                              24

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GTTGCACTCC TGTTTCACGG TCTG                                              24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CAAGACACCT TGAAGGGCCT GATG                                              24

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TAACTTTTAC AGAAGAGCAT CAGC                                              24

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

AGCGCGGCCG CATGAACAAG TGGCTGTGCT GCG                                    33

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AGCTCTAGAG AAACAGCCCA GTGACCATTC C                           31

(2) INFORMATION FOR SEQ ID NO:25:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:25:

GTGAAGCTGT GCAAGAACCT GATG                                   24

(2) INFORMATION FOR SEQ ID NO:26:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:26:

ATCAAAGGCA GGGCATACTT CCTG                                   24

(2) INFORMATION FOR SEQ ID NO:27:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:27:

TCCGTAAGAA ACAGCCCAGT GACC                                   24

(2) INFORMATION FOR SEQ ID NO:28:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:28:

CAGATCCTGA AGCTGCTCAG TTTG                                   24

(2) INFORMATION FOR SEQ ID NO:29:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:29:

AGCGCGGCCG CGGGGACCAC AATGAACAAG TTG                          33

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

AGCTCTAGAA TTGTGAGGAA ACAGCTCAAT GGC                          33

(2) INFORMATION FOR SEQ ID NO:31:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CCTCTGAGCT CAAGCTTCCG AGGACCACAA TGAACAAG                     38

(2) INFORMATION FOR SEQ ID NO:32:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

CCTCTGCGGC CGCTAAGCAG CTTATTTTCA CGGATTGAAC CTG               43

(2) INFORMATION FOR SEQ ID NO:33:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

CCTCTGAGCT CAAGCTTCCG AGGACCACAA TGAACAAG                     38

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CCTCTGCGGC CGCTGTTGCA TTTCCTTTCT G                            31

(2) INFORMATION FOR SEQ ID NO:35:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Glu Thr Leu Pro Pro Lys Tyr Leu His Tyr Asp Pro Glu Thr Gly His
1               5                   10                  15

Gln Leu Leu
```

(2) INFORMATION FOR SEQ ID NO:36:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
TACGCACTGG ATCCTTATAA GCAGCTTATT TTTACTGATT GGAC                    44
```

(2) INFORMATION FOR SEQ ID NO:37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
GTCCTCCTGG TACCTACCTA AAACAAC                                       27
```

(2) INFORMATION FOR SEQ ID NO:38:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

```
TATGGATGAA GAAACTTCTC ATCAGCTGCT GTGTGATAAA TGTCCGCCGG GTAC          54
```

(2) INFORMATION FOR SEQ ID NO:39:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

```
CCGGCGGACA TTTATCACAC AGCAGCTGAT GAGAAGTTTC TTCATCCA                48
```

(2) INFORMATION FOR SEQ ID NO:40:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

Met Tyr Asp Glu Glu Thr Ser His Gln Leu Leu Cys Asp Lys Cys Pro
1               5                   10                  15

Pro Gly Thr (2) INFORMATION FOR SEQ ID NO:41:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Ala Leu Leu Val Phe Leu Asp Ile Ile Glu Trp Thr Thr Gln Glu Thr
1               5                   10                  15

Phe Pro Pro Lys Tyr Leu His Tyr Asp Pro Glu Thr Gly Arg Gln Leu
                20                  25                  30

Leu Cys Asp Lys Cys Ala Pro Gly Thr Tyr Leu Lys Gln His Cys Thr
                35                  40                  45

Val Arg Arg Lys Thr Leu Cys Val Pro Cys Pro Asp Tyr Ser Tyr Thr
50                  55                  60

Asp Ser Trp His Thr Ser
65                  70

(2) INFORMATION FOR SEQ ID NO:42:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

His Ala Leu Pro Ala Gln Val Ala Phe Thr Pro Tyr Ala Pro Glu Pro
1               5                   10                  15

Gly Ser Thr Cys Arg Leu Arg Glu Tyr Tyr Asp Gln Thr Ala Gln Met
                20                  25                  30

Cys Cys Ser Lys Cys Ser Pro Gly Gln His Ala Lys Val Phe Cys Thr
                35                  40                  45

Lys Thr Ser Asp Thr Val Cys Asp Ser Cys Glu Asp Ser Thr Tyr Thr
50                  55                  60

Gln Leu Trp Asn Trp Val Pro Glu Cys Leu Ser Cys Gly Ser Arg Cys
65                  70                  75                  80

Ser Ser Asp Gln Val Glu Thr Gln Ala Cys Thr Arg Glu Gln Asn Arg
                85                  90                  95

Ile Cys Thr Cys Arg Pro Gly Trp Tyr Cys Ala Leu Ser Lys Gln Glu
                100                 105                 110

Gly Cys Arg Leu Cys Ala Pro Leu

```
                115                 120
```

(2) INFORMATION FOR SEQ ID NO:43:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Tyr Leu His Tyr Asp Pro Glu Thr Gly Arg Gln Leu Leu Cys Asp Lys
1               5                  10                  15

Cys Ala Pro Gly Thr Tyr Leu Lys Gln His Cys Thr Val Arg Arg Lys
            20                  25                  30

Thr Leu Cys Val Pro Cys Pro Asp Tyr Ser Tyr Thr Asp Ser Trp His
        35                  40                  45
```

(2) INFORMATION FOR SEQ ID NO:44:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Tyr His Tyr Tyr Asp Gln Asn Gly Arg Met Cys Glu Glu Cys His Met
1               5                  10                  15

Cys Gln Pro Gly His Phe Leu Val Lys His Cys Lys Gln Pro Lys Arg
            20                  25                  30

Asp Thr Val Cys His Lys Pro Cys Glu Pro Gly Val Thr Tyr Thr Asp
        35                  40                  45

Asp Trp His
    50
```

(2) INFORMATION FOR SEQ ID NO:45:

(i) SEQUENCE CHARACTERISTICS:
        (A) LENGTH: 219 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Met Leu Gly Ile Trp Thr Leu Leu Pro Leu Val Leu Thr Ser Val Ala
1               5                  10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
            35                  40                  45

Leu Glu Gly Leu His His Asp Gly Gln Phe Cys His Lys Pro Cys Pro
        50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
            85                  90                  95
```

```
Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
        130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr
    210                 215
```

(2) INFORMATION FOR SEQ ID NO:46:

(i) SEQUENCE CHARACTERISTICS:
        (A) LENGTH: 280 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220
```

```
Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr
            275                 280
```

(2) INFORMATION FOR SEQ ID NO:47:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
Met Leu Arg Leu Ile Ala Leu Leu Val Cys Val Val Tyr Val Tyr Gly
1               5                   10                  15

Asp Asp Val Pro Tyr Ser Ser Asn Gln Gly Lys Cys Gly Gly His Asp
            20                  25                  30

Tyr Glu Lys Asp Gly Leu Cys Cys Ala Ser Cys His Pro Gly Phe Tyr
            35                  40                  45

Ala Ser Arg Leu Cys Gly Pro Gly Ser Asn Thr Val Cys Ser Pro Cys
50                  55                  60

Glu Asp Gly Thr Phe Thr Ala Ser Thr Asn His Ala Pro Ala Cys Val
65                  70                  75                  80

Ser Cys Arg Gly Pro Cys Thr Gly His Leu Ser Glu Ser Gln Pro Cys
                85                  90                  95

Asp Arg Thr His Asp Arg Val Cys Asn Cys Ser Thr Gly Asn Tyr Cys
            100                 105                 110

Leu Leu Lys Gly Gln Asn Gly Cys Arg Ile Cys Ala Pro Gln Thr Lys
            115                 120                 125

Cys Pro Ala Gly Tyr Gly Val Ser Gly His Thr Arg Ala Gly Asp Thr
130                 135                 140

Leu Cys Glu Lys Cys Pro Pro His Thr Tyr Ser Asp Ser Leu Ser Pro
145                 150                 155                 160

Thr Glu Arg Cys Gly Thr Ser Phe Asn Tyr Ile Ser Val Gly Phe Asn
                165                 170                 175

Leu Tyr Pro Val Asn Glu Thr Ser Cys Thr Thr Thr Ala Gly His Asn
            180                 185                 190

Glu Val Ile Lys Thr Lys Glu Phe Thr Val Thr Leu Asn Tyr Thr
            195                 200                 205
```

(2) INFORMATION FOR SEQ ID NO:48:

(i) SEQUENCE CHARACTERISTICS:
        (A) LENGTH: 227 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Met Ala Pro Val Ala Val Trp Ala Ala Leu Ala Val Gly Leu Glu Leu

```
 1               5                   10                  15
Trp Ala Ala His Ala Leu Pro Ala Gln Val Ala Phe Thr Pro Tyr
                20                  25                  30
Ala Pro Glu Pro Gly Ser Thr Cys Arg Leu Arg Glu Tyr Tyr Asp Gln
            35                  40                  45
Thr Ala Gln Met Cys Cys Ser Lys Cys Ser Pro Gly Gln His Ala Lys
 50                  55                  60
Val Phe Cys Thr Lys Thr Ser Asp Thr Val Cys Asp Ser Cys Glu Asp
 65                  70                  75                  80
Ser Thr Tyr Thr Gln Leu Trp Asn Trp Val Pro Glu Cys Leu Ser Cys
                85                  90                  95
Gly Ser Arg Cys Ser Ser Asp Gln Val Glu Thr Gln Ala Cys Thr Arg
            100                 105                 110
Glu Gln Asn Arg Ile Cys Thr Cys Arg Pro Gly Trp Tyr Cys Ala Leu
            115                 120                 125
Ser Lys Gln Glu Gly Cys Arg Leu Cys Ala Pro Leu Arg Lys Cys Arg
 130                 135                 140
Pro Gly Phe Gly Val Ala Arg Pro Gly Thr Glu Thr Ser Asp Val Val
 145                 150                 155                 160
Cys Lys Pro Cys Ala Pro Gly Thr Phe Ser Asn Thr Thr Ser Ser Thr
            165                 170                 175
Asp Ile Cys Arg Pro His Gln Ile Cys Asn Val Val Ala Ile Pro Gly
            180                 185                 190
Asn Ala Ser Arg Asp Ala Val Cys Thr Ser Thr Ser Pro Thr Arg Ser
            195                 200                 205
Met Ala Pro Gly Ala Val His Leu Pro Gln Pro Val Ser Thr Arg Ser
            210                 215                 220
Gln His Thr
225

(2) INFORMATION FOR SEQ ID NO:49:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

Met Val Ser Leu Pro Arg Leu Cys Ala Leu Trp Gly Cys Leu Leu Thr
 1               5                   10                  15
Ala Val His Leu Gly Gln Cys Val Thr Cys Ser Asp Lys Gln Tyr Leu
                20                  25                  30
His Asp Gly Gln Cys Cys Asp Leu Cys Gln Pro Gly Ser Arg Leu Thr
            35                  40                  45
Ser His Cys Thr Ala Leu Glu Lys Thr Gln Cys His Pro Cys Asp Ser
 50                  55                  60
Gly Glu Phe Ser Ala Gln Trp Asn Arg Glu Ile Arg Cys His Gln His
 65                  70                  75                  80
Arg His Cys Glu Pro Asn Gln Gly Leu Arg Val Lys Lys Glu Gly Thr
            85                  90                  95
Ala Glu Ser Asp Thr Val Cys Thr Cys Lys Glu Gly Gln His Cys Thr
            100                 105                 110
Ser Lys Asp Cys Glu Ala Cys Ala Gln His Thr Pro Cys Ile Pro Gly
```

```
            115                 120                 125
Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val
            195

(2) INFORMATION FOR SEQ ID NO:50:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
            130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
210                 215                 220

(2) INFORMATION FOR SEQ ID NO:51:

(i) SEQUENCE CHARACTERISTICS:
        (A) LENGTH: 205 amino acids
        (B) TYPE: amino acid
        (C) STRANDEDNESS: single
```

(D) TOPOLOGY: linear (ii) MOLECULE TYPE: protein (xi) SEQUENCE DESCRIPTION: SEQ ID NO:51:

Met Tyr Val Trp Val Gln Gln Pro Thr Ala Phe Leu Leu Gly Leu
1               5                   10                  15

Ser Leu Gly Val Thr Val Lys Leu Asn Cys Val Lys Asp Thr Tyr Pro
            20                  25                  30

Ser Gly His Lys Cys Cys Arg Glu Cys Gln Pro Gly His Gly Met Val
            35                  40                  45

Ser Arg Cys Asp His Thr Arg Asp Thr Val Cys His Pro Cys Glu Pro
        50                  55                  60

Gly Phe Tyr Asn Glu Ala Val Asn Tyr Asp Thr Cys Lys Gln Cys Thr
65                  70                  75                  80

Gln Cys Asn His Arg Ser Gly Ser Glu Leu Lys Gln Asn Cys Thr Pro
                85                  90                  95

Thr Glu Asp Thr Val Cys Gln Cys Arg Pro Gly Thr Gln Pro Arg Gln
            100                 105                 110

Asp Ser His Lys Leu Gly Val Asp Cys Val Pro Cys Pro Pro Gly
        115                 120                 125

His Phe Ser Pro Gly Ser Asn Gln Ala Cys Lys Pro Trp Thr Asn Cys
130                 135                 140

Thr Leu Ser Gly Lys Gln Ile Arg His Pro Ala Ser Asn Ser Leu Asp
145                 150                 155                 160

Thr Val Cys Glu Asp Arg Ser Leu Leu Ala Thr Leu Leu Trp Glu Thr
                165                 170                 175

Gln Arg Thr Thr Phe Arg Pro Thr Thr Val Pro Ser Thr Thr Val Trp
            180                 185                 190

Pro Arg Thr Ser Gln Leu Pro Ser Thr Pro Thr Leu Val
        195                 200                 205

(2) INFORMATION FOR SEQ ID NO:52:

(i) SEQUENCE CHARACTERISTICS:
          (A) LENGTH: 191 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:52:

Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
        50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

-continued

```
Lys Gln Gly Cys Lys Thr Cys Ser Leu Gly Thr Phe Asn Asp Gln Asn
            115                 120                 125

Gly Thr Gly Val Cys Arg Pro Trp Thr Asn Cys Ser Leu Asp Gly Arg
        130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu
            180                 185                 190
```

(2) INFORMATION FOR SEQ ID NO:53:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Thr Ala Thr Gly Gly Ala Thr Gly Ala Ala Gly Ala Ala Ala Cys Thr
1               5                   10                  15

Thr Cys Thr Cys Ala Thr Cys Ala Gly Cys Thr Gly Cys Thr Gly Thr
            20                  25                  30

Gly Thr Gly Ala Thr Ala Ala Thr Gly Thr Cys Cys Gly Cys Cys Cys
            35                  40                  45

Gly Gly Gly Thr Ala Cys Ala Cys Cys Thr Ala Cys Thr Thr Cys Thr
        50                  55                  60

Thr Thr Gly Ala Ala Gly Ala Gly Thr Ala Gly Thr Cys Gly Ala Cys
65                  70                  75                  80

Gly Ala Cys Ala Cys Ala Cys Thr Ala Thr Thr Thr Ala Cys Ala Gly
            85                  90                  95

Gly Cys Gly Gly Cys Cys
            100
```

US 6,284,485 B1

NUCLEIC ACIDS ENCODING OSTEOPROTEGERIN

This application is a division of application Ser. No. 08/577,788, filed Dec. 22, 1995, pending.

FIELD OF THE INVENTION

The invention relates generally to polypeptides involved in the regulation of bone metabolism. More particularly, the invention relates to a novel polypeptide, termed osteoprotegerin, which is a member of the tumor necrosis factor receptor superfamily. The polypeptide is used to treat bone diseases characterized by increased bone loss such as osteoporosis.

BACKGROUND OF THE INVENTION

Polypeptide growth factors and cytokines are secreted factors which signal a wide variety of changes in cell growth, differentiation, and metabolism, by specifically binding to discrete, surface bound receptors. As a class of proteins, receptors vary in their structure and mode of signal transduction. They are characterized by having an extracellular domain that is involved in ligand binding, and cytoplasmic domain which transmits an appropriate intracellular signal. Receptor expression patterns ultimately determine which cells will respond to a given ligand, while the structure of a given receptor dictates the cellular response induced by ligand binding. Receptors have been shown to transmit intracellular signals via their cytoplasmic domains by activating protein tyrosine, or protein serine/threonine phosphorylation (e.g., platelet derived growth factor receptor (PDGFR) or transforming growth factor-β receptor -I (TGFβR-I), by stimulating G-protein activation (e.g., β-adrenergic Receptor), and by modulating associations with cytoplasmic signal transducing proteins (e.g., TNFR-1 and Fas/APO) (Heldin, Cell 80, 213–223 (1995)).

The tumor necrosis factor receptor (TNFR) superfamily is a group of type I transmembrane proteins which share a conserved cysteine-rich motif which is repeated three to six times in the extracellular domain (Smith, et al. Cell 76, 953–962 (1994)). Collectively, these repeat units form the ligand binding domains of these receptors (Chen et al., Chemistry 270, 2874–2878 (1995)). The ligands for these receptors are a structurally related group of proteins homologous to TNFa. (Goeddel et al. Cold Spring Harbor Symp. Quart. Biol. 51, 597–609 (1986); Nagata et al. Science 27, 1449–1456 (1995)). TNFα binds to distinct, but closely related receptors, TNFR-1 and TNFR-2. TNFα produces a variety of biological responses in receptor bearing cells, including, proliferation, differentiation, and cytotoxicity and apoptosis (Beutler et al. Ann. Rev. Biochem. 5, 505–518 (1988)).

TNFα is believed to mediate acute and chronic inflammatory responses (Beutler et al. Ann. Rev. Biochem. 57, 505–508 (1988)). Systemic delivery of TNFα induces toxic shock and widespread tissue necrosis. Because of this, TNFα may be responsible for the severe morbidity and mortality associated with a variety of infectious diseases, including sepsis. Mutations in FasL, the ligand for the TNFR-related receptor Fas/APO (Suda et al. Cell, 1169–1178 (1993)), is associated with autoimmunity (Fisher et al. Cell 81, 935–946 (1995)), while overproduction of FasL may be implicated in drug-induced hepatitis. Thus, ligands to the various TNFR-related proteins often mediate the serious effects of many disease states, which suggests that agents that neutralize the activity of these ligands would have therapeutic value. Soluble TNFR-1 receptors, and antibodies that bind TNFα, have been tested for their ability to neutralize systemic TNFα (Loetscher et al. Cancer Cells 3, 221–226 (1991)). A naturally occuring form of a secreted TNFR-1 mRNA was recently cloned, and its product tested for its ability to neutralize TNFα activity in vitro and in vivo (Kohno et al. PNAS USA 87, 8331–8335 (1990)). The ability of this protein to neutralize TNFα suggests that soluble TNFA receptors function to bind and clear TNF thereby blocking the cytotoxic effects on TNFR- bearing cells.

An object of the invention to identify new members of the TNFR super family. It is anticipated that new family members, may be transmembrane proteins or soluble forms thereof comprising extracellular domains and lacking transmembrane and cytoplasmic domains. We have identified a new member of the TNFR superfamily which encodes a secreted protein that is closely related to TNFR-2. By analogy to soluble TNFR-1, the TNFR-2 related protein may negatively regulate the activity of its ligand, and thus may be useful in the treatment of certain human diseases.

SUMMARY OF THE INVENTION

A novel member of the tumor necrosis factor receptor (TNFR) superfamily has been identified from a fetal rat intestinal cDNA library. A full-length cDNA clone was obtained and sequenced. Expression of the rat cDNA in a transgenic mouse revealed a marked increase in bones density, particularly in long bones, pelvic bone and vertebrae. The polypeptide encoded by the CDNA is termed osteoprotegerin and plays a role in promoting bone accumulation.

The invention provides for nucleic acids encoding a polypeptide having at least one of the biological activities of osteoprotegerin. Nucleic acids which hybridize to nucleic acids encoding mouse, rat or human Osteoprotegerin as shown in FIGS. 2B, 9A and 9B are also provided. Preferably, osteoprotegerin is mammalian osteoprotegerin and more preferably is human osteoprotegerin. Recombinant vectors and host cells expressing osteoprotegerin are also encompassed as are methods of producing recombinant osteoprotegerin. Antibodies or fragments thereof which specifically bind the polypeptide are also disclosed.

Methods of treating bone diseases are also provided by the invention. The polypeptides are useful for preventing bone resorption and may be used to treat any condition resulting in bone loss such as osteoporosis, hypercalcemia, Paget's disease of bone, and bone loss due to rheumatoid arthritis or osteomyelitis, and the like. Bone diseases may also be treated with anti-sense or gene therapy using nucleic acids of the invention. Pharmaceutical compositions comprising osteoprotegerin nucleic acids and polypeptides are also encompassed.

DESCRIPTION OF THE FIGURES

FIG. 2. Structure and sequence of full length rat Osteoprotegerin gene (SEQ ID NO: 1), a novel member of the TNFR superfamily. A. Map of pMOB-B1.1 insert. Box indicates position of LORF within the cDNA sequence (bold line). Black box indicates signal peptide, and gray ellipses indicate position of cysteine-rich repeat sequences. B. Nucleic acid (SEQ ID NO: 1) and protein (SEQ ID NO: 2) sequence of the Rat Osteoprotegerin cDNA. The predicted signal peptide is underlined, and potential sites of N-linked glycosylation are indicated in bold, underlined letters. C. Pileup sequence comparison (Wisconsin GCG Package, Version 8.1) of Osteoprotegerin (SEQ ID NO: 2) with other members of the TNFR superfamily (SEQ ID NO: 45–52).

FIG. 3. PepPlot analysis (Wisconsin GCG Package, Version 8.1) of the predicted rat Osteoprotegerin protein sequence.

FIG. 4. mRNA expression patterns for the Osteoprotegerin cDNA in human tissues. Northern blots were probed with a 32P-labeled rat cDNA insert (left two panels), or with the human cDNA insert (right panel).

FIG. 9. Structure and sequence of mouse and human Osteoprotegerin cDNA clones. A. Mouse CDNA (SEQ ID NO: 3) and protein (SEQ ID NO: 4) sequence. B. Human cDNA (SEQ ID NO: 5) and protein (SEQ ID NO: 6) sequence. The predicted signal peptides are underlined, and potential sites of N-linked glycosylation are indicated in bold. C. Sequence alignment and comparison of rat (SEQ ID NO: 2), mouse (SEQ ID NO: 4) and human (SEQ ID NO: 6) Osteoprotegerin amino acid sequences.

DETAILED DESCRIPTION OF THE INVENTION

Figure 1C:
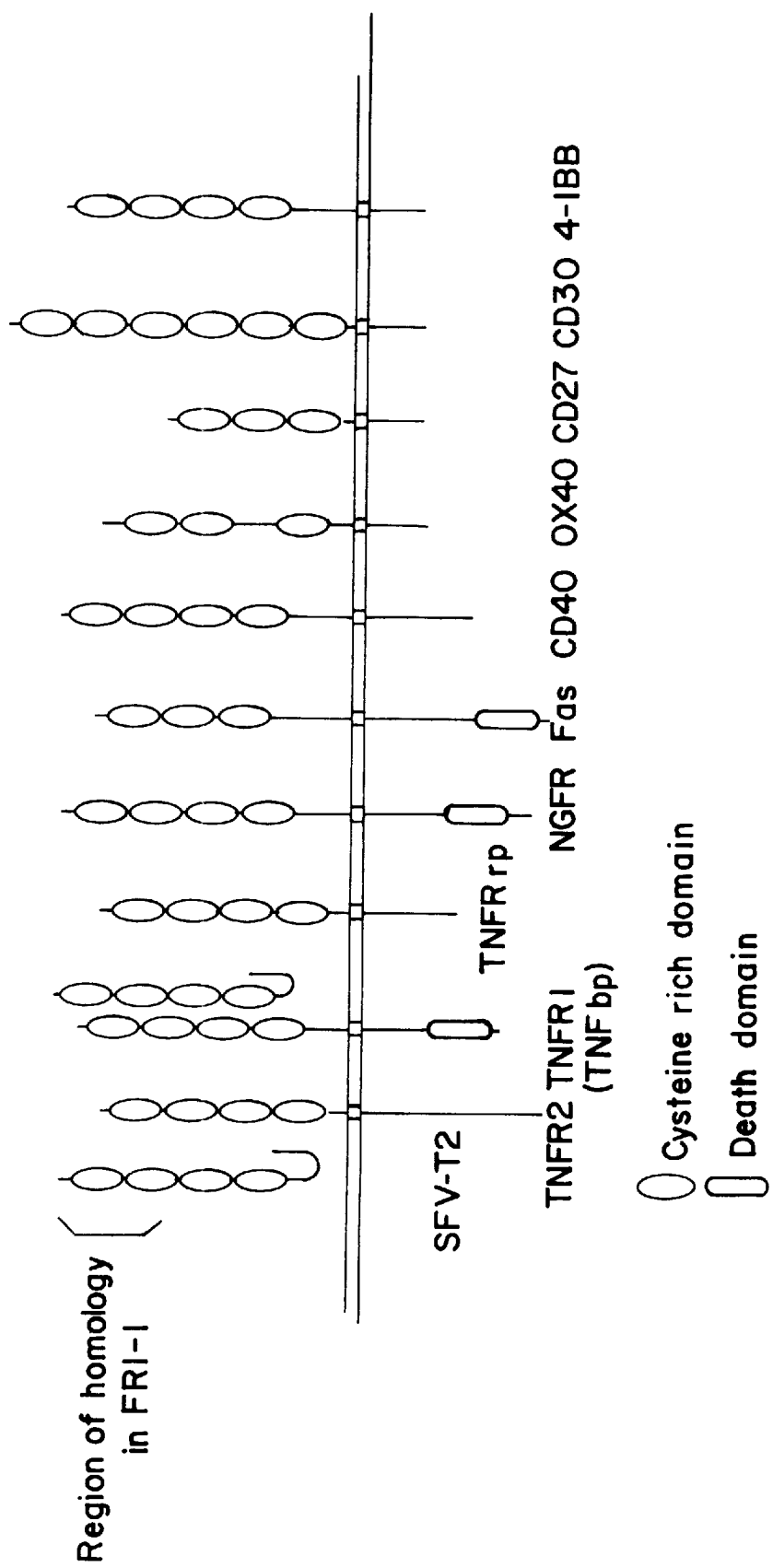
FIG. 1. A. FASTA analysis of novel EST LORF. Shown is the deduced FRI-1 amino acid sequence (SEQ ID NO: 41) aligned to the human TNFR-2 sequence (SEQ ID NO: 42). B. Profile analysis of the novel EST LORF shown is the deduced FRI-1 amino acid sequence (SEQ ID NO: 43) aligned to the TNFR-profile (SEQ ID NO: 44). C. Structural view of TNFR superfamily indicating region which is homologous to the novel FRI-1.
Figure 2D:
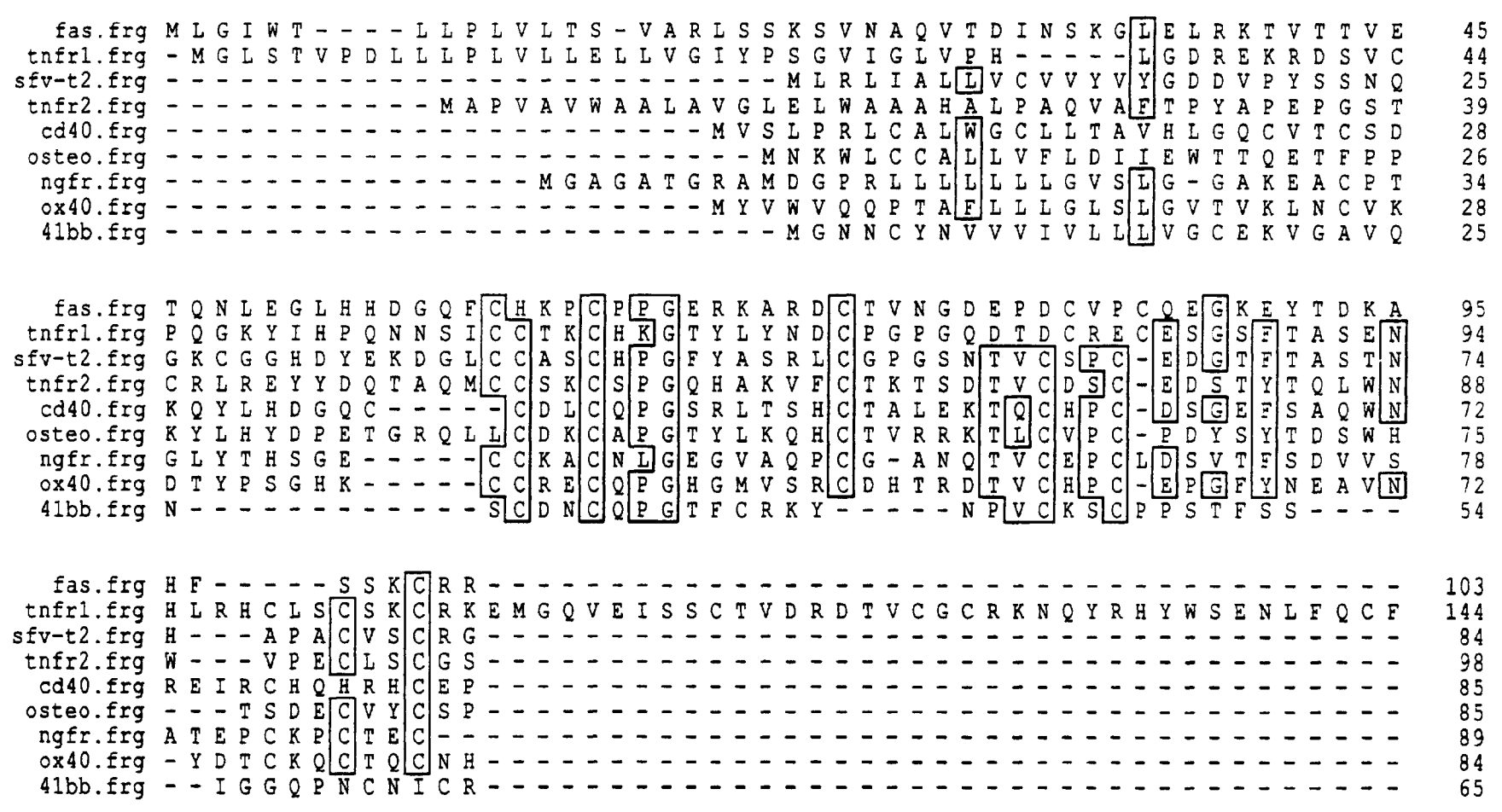
Figure 2E:
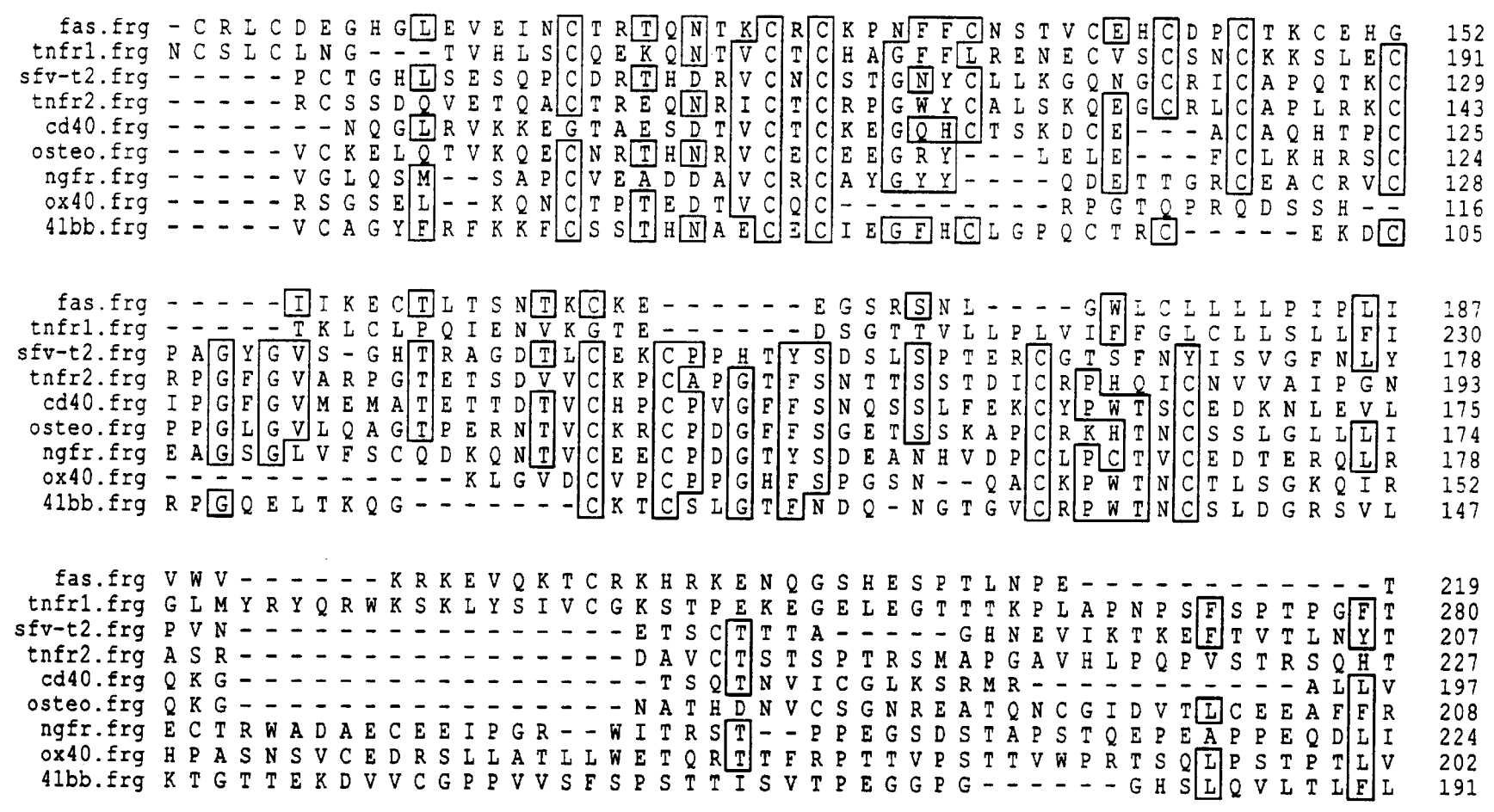
Figure 5:
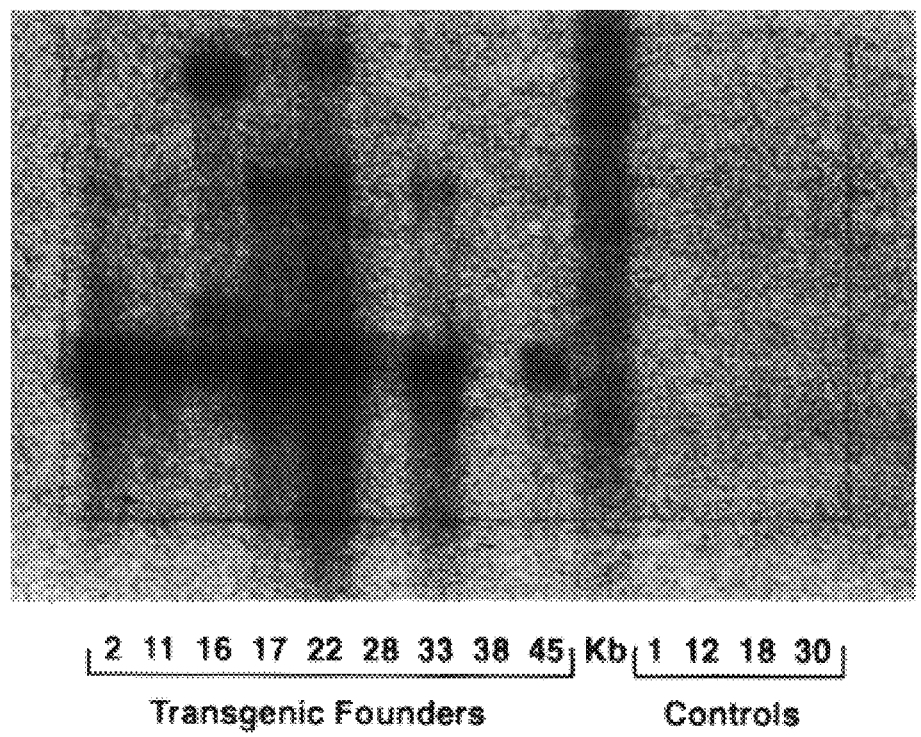
FIG. 5. Creation of transgenic mice expressing the Osteoprotegerin cDNA in hepatocytes. Northern blot expression of HE-Osteoprotegerin transgene in mouse liver.
Figure 6A:
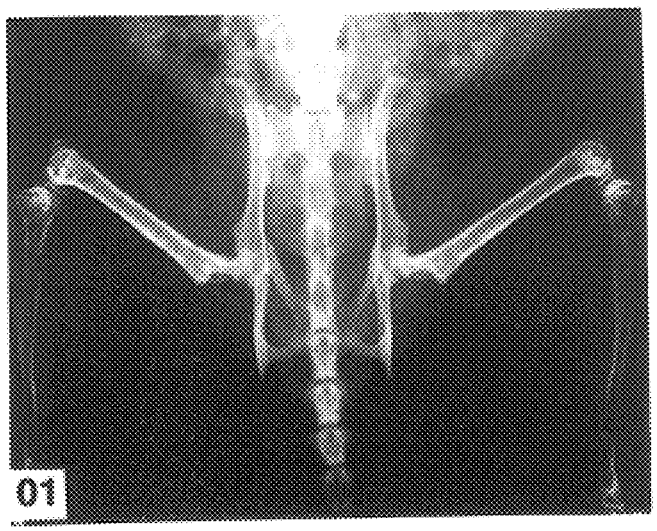
FIG. 6. Increase in bone density in Osteoprotegerin transgenic mice. Panel A. Control Mice. Panel B, Osteoprotegerin expressing mice. At necropsy, all animals were radiographed and photographs prepared. In A, the radiographs of the control animals and the one transgenic non-expressor (#28) are shown. Note that the bones have a clearly defined cortex and a lucent central marrow cavity. In contrast, the Osteoprotegerin (B) animals have a poorly defined cortex and increased density in the marrow zone.
Figure 6B:
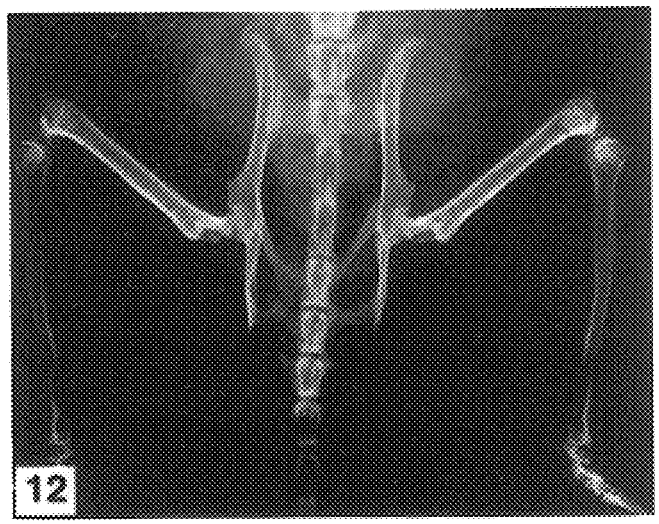
Figure 6C:
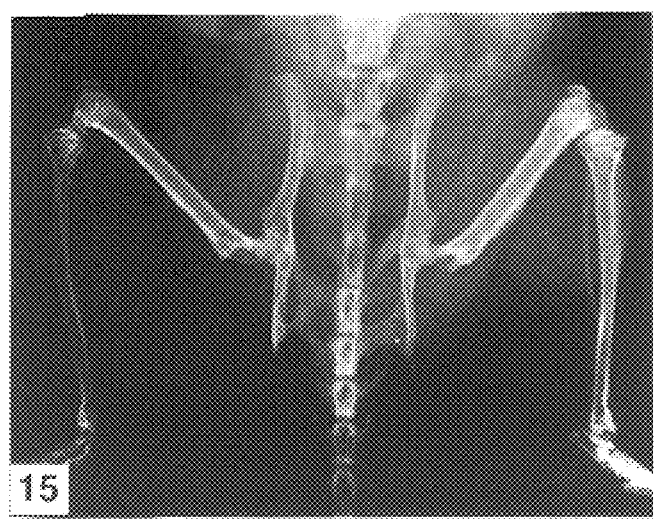
Figure 6D:
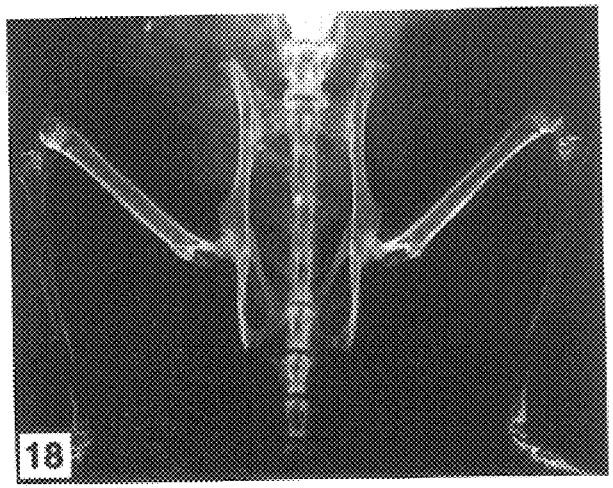
Figure 6E:
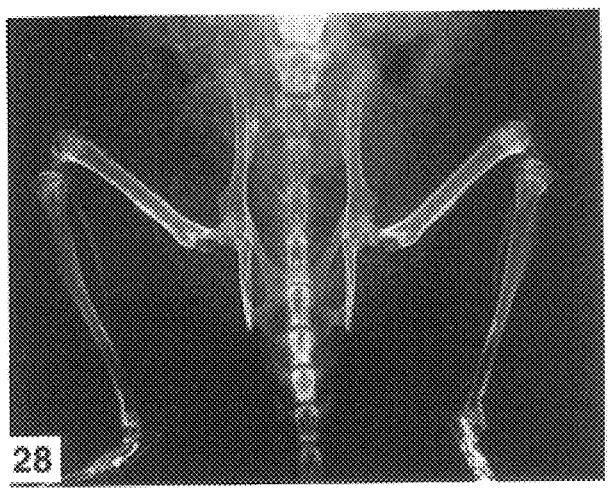
Figure 6F:
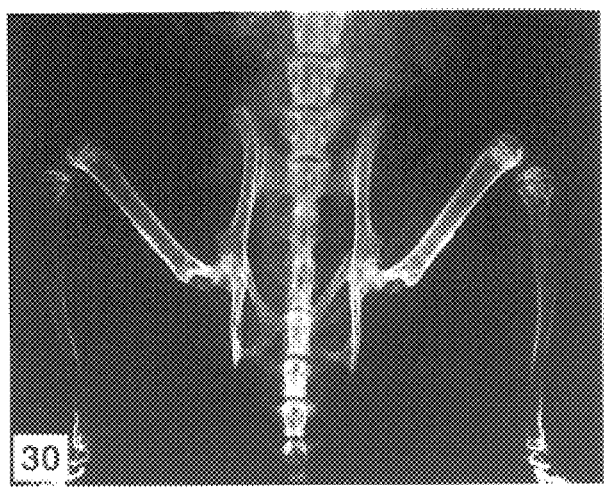
Figure 6G:
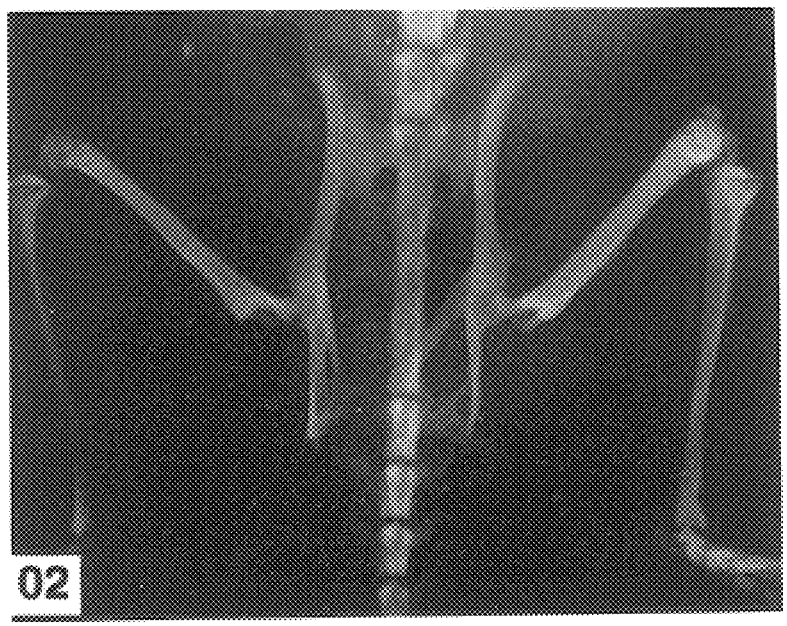
Figure 6H:
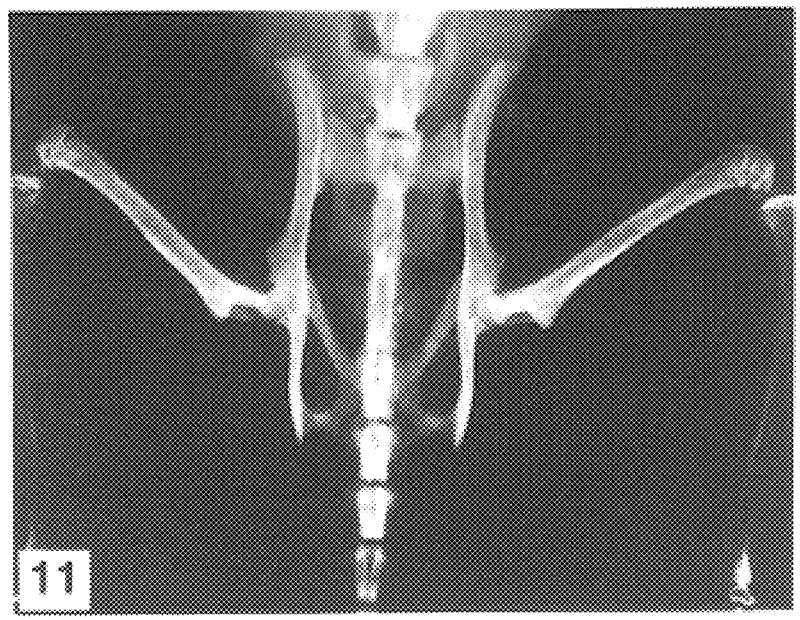
Figure 6I:
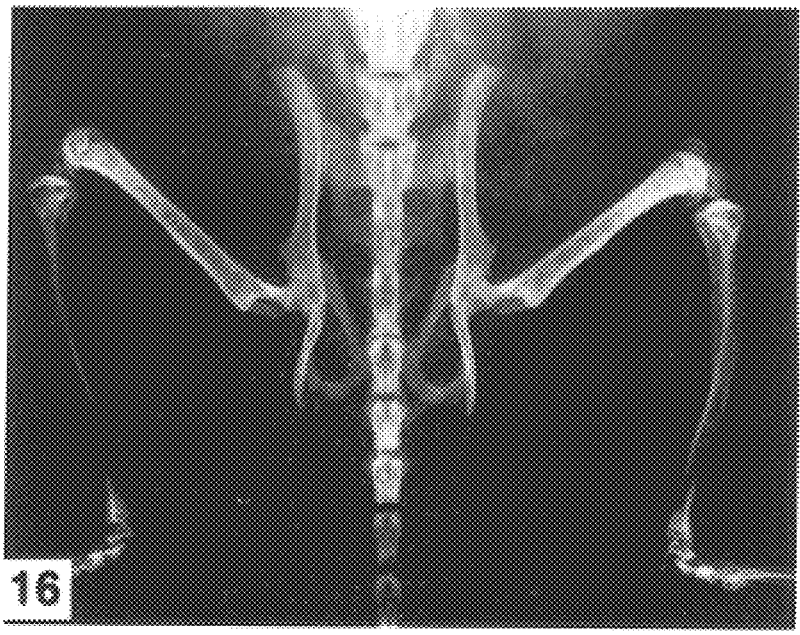
Figure 6J:
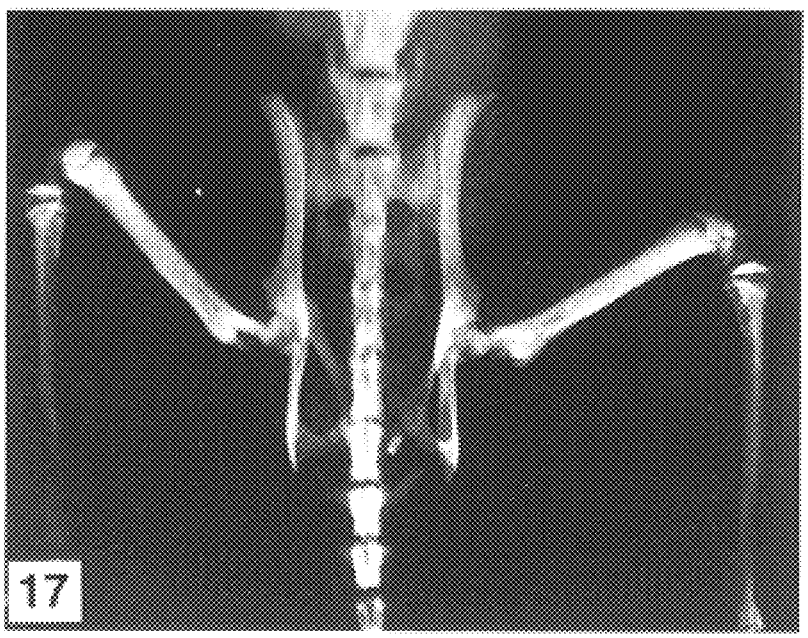
Figure 7A:
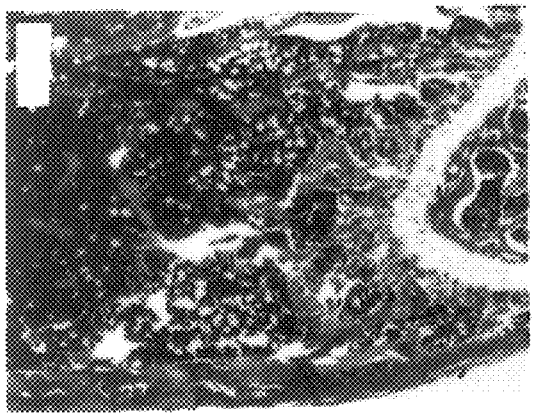
FIG. 7. Increase in trabecular bone in Osteoprotegerin transgenic mice. Plate A. Representative photomicrographs of bones from control animals. In A and B, low (4x, 10x) power images of the femurs are shown (Masson Trichrome stain). Stains for tartrate resistant acid phosphatase (TRAP) demonstrate osteoclasts (see arrows) both resorbing cartilage (C) and trabecular bone (D). Note the flattened appearance of osteoclasts on trabecular bone. Plate B. Representative photomicrographs of bones from Osteoprotegerin-expressing animals. In A and B, low (4x, 10x) power images of the femurs are shown (Masson Trichrome stain). The clear region is the growth plate cartilage, blue stained area is bone, and the red area is marrow. Note that in contrast to the controls, the trabecular bone has not been resorbed resulting in the absence of the usual marrow cavity. Also, the resulting trabeculae have a variegated appearance with blue and clear areas. The clear areas are remnants of growth plate cartilage that have never been remodelled. Based on TRAP stains, these animals do have osteoclasts (see arrows) at the growth plate (panel C), which may be reduced in number. However, the surfaces of the trabeculae away from the growth plate are virtually devoid of osteoclasts (D), a finding that stands in direct contrast with the control animals (see Plate A,. Panal D).
Figure 7B:
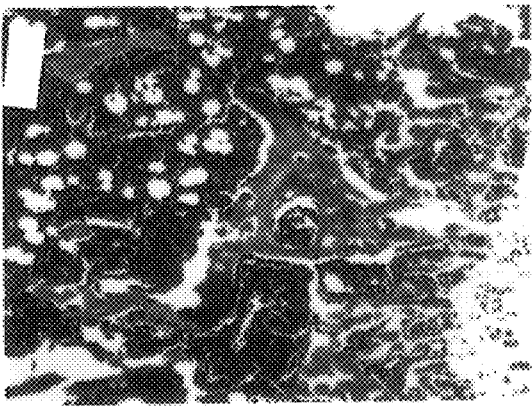
Figure 7C:
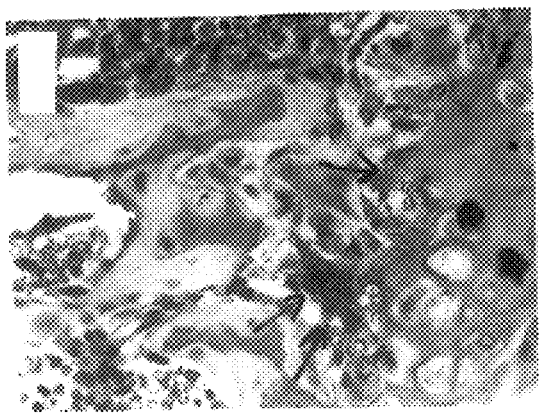
Figure 7D:
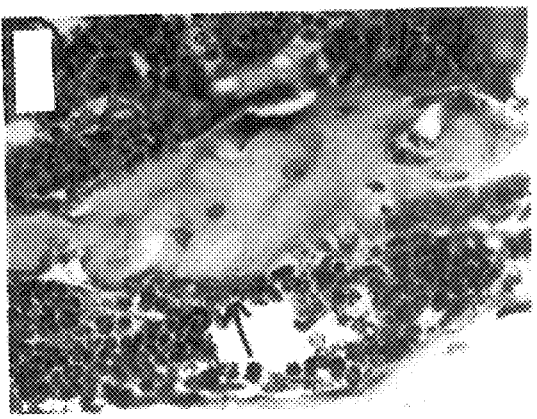
Figure 7E:
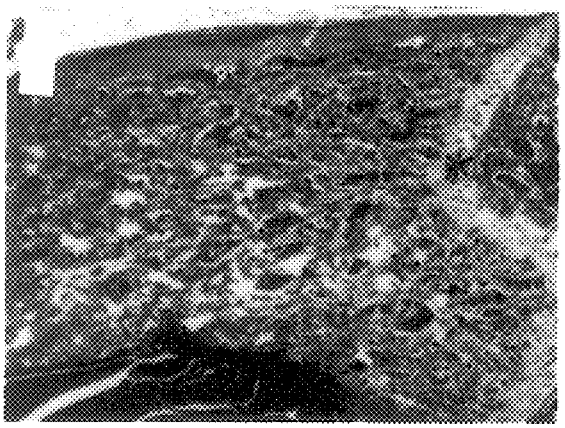
Figure 7F:
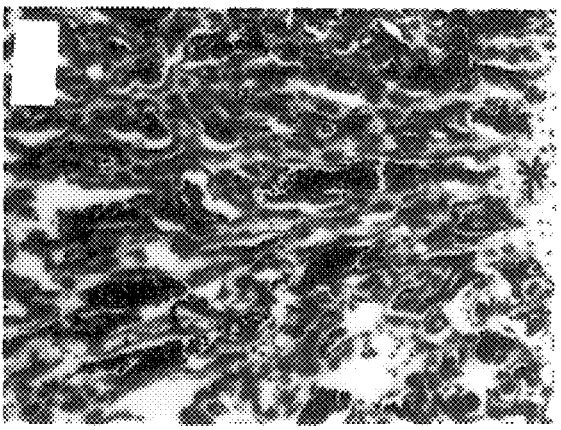
Figure 7G:
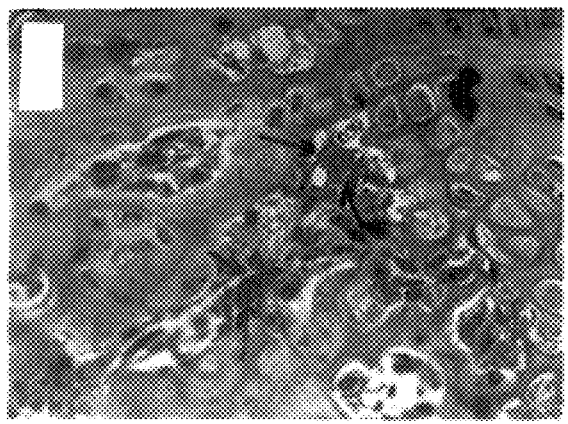
Figure 7H:
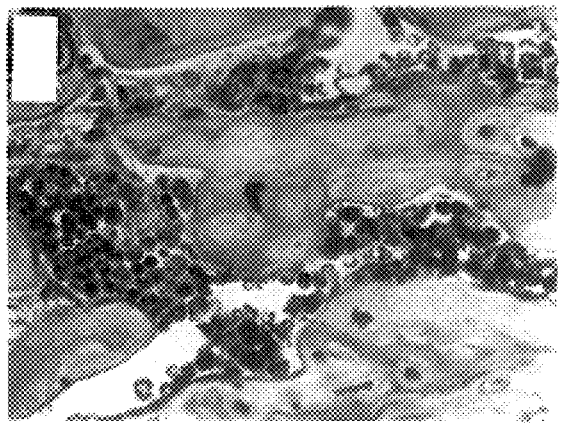
Figure 8A:
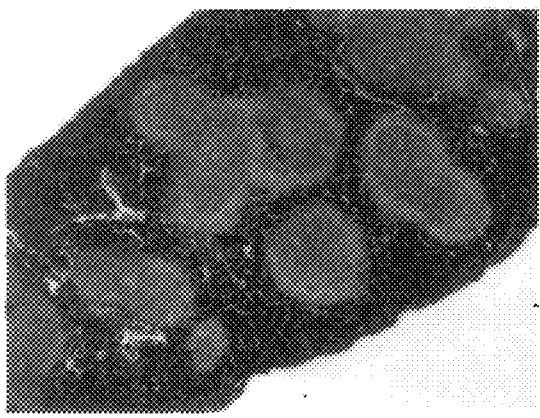
FIG. 8. HE-Osteoprotegerin expressors do not have a defect in monocyte-macrophage development. One cause for osteopetrosis in mice is defective M-CSF production due to a point mutation in the M-CSF gene. This results in a marked deficit of circulating and tissue based macrophages. The peripheral blood of Osteoprotegerin expressors contained monocytes as assessed by H1E analysis. To affirm the presence of tissue macrophages, immnohistochemistry was performed using F480 antibodies, which recognize a cell surface antigen on murine macrophages. Panels A and C show low power (4x) photomicrographs of the spleens from normal and CR1 overexpressors. Note that both animals have numerous F480 positive cells. Monocyte-macrophages were also present in the marrow of normal (B) and HE-Osteoprotegerin overexpressors (D) (40x).
Figure 8B:
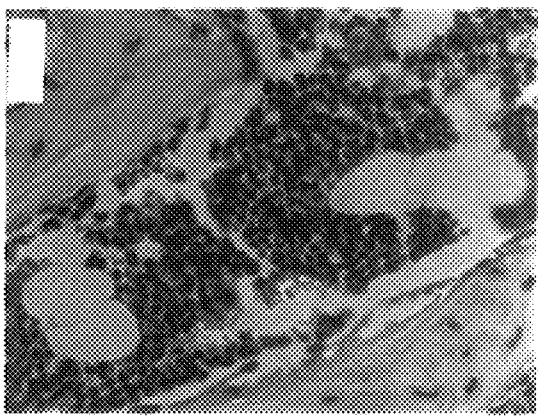
Figure 8C:
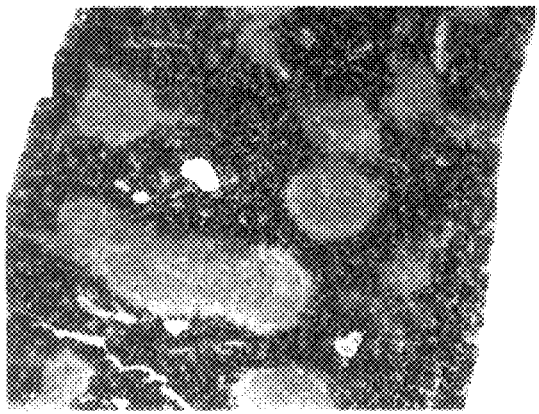
Figure 8D:
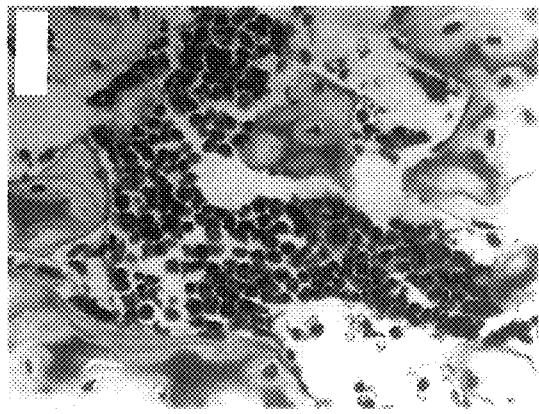
Figure 10A:
FIG. 10. Expression and secretion of full length and truncated mouse Osteoprotegerin-Fc fusion proteins. A. Map indicating points of fusion to the human IgG1 Fc domain are indicated by arrowheads. B. Silver stain of and SDS-polyacrylamide gel of conditioned media obtained from F1.Fc (Full length Osteoprotegerin fused to Fc at Leucine 401) and CT.Fc (Carboxy-terminal truncated osteoprotegerin fused to Fc at threonine 180) fusion protein expression vectors. Lane 1, parent pCEP4 expression vector cell line; Lane 2, F1.Fc vector cell line; Lane 3, CT.Fc vector cell line. C. Western blot of conditioned media obtained from Fl.Fc and CT.Fc fusion protein expression vectors probed with anti-human IgGl Fc domain (Pierce). Lane 1, parent pCEP4 expression vector cell line; Lane 2, F1.Fc vector cell line; Lane 3, CT.Fc vector cell line.
Figure 10B:
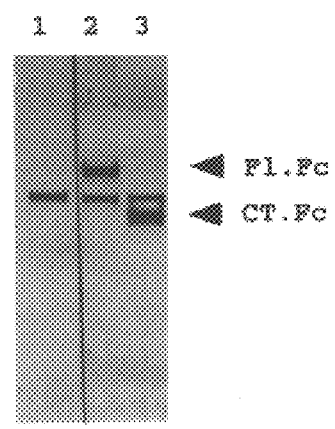
Figure 10C:
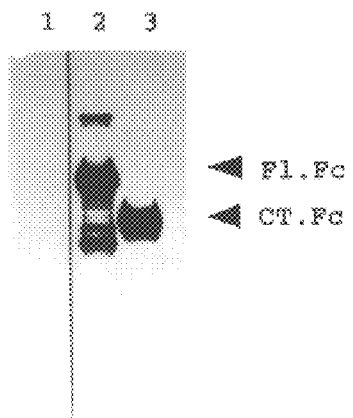
Figure 11A:
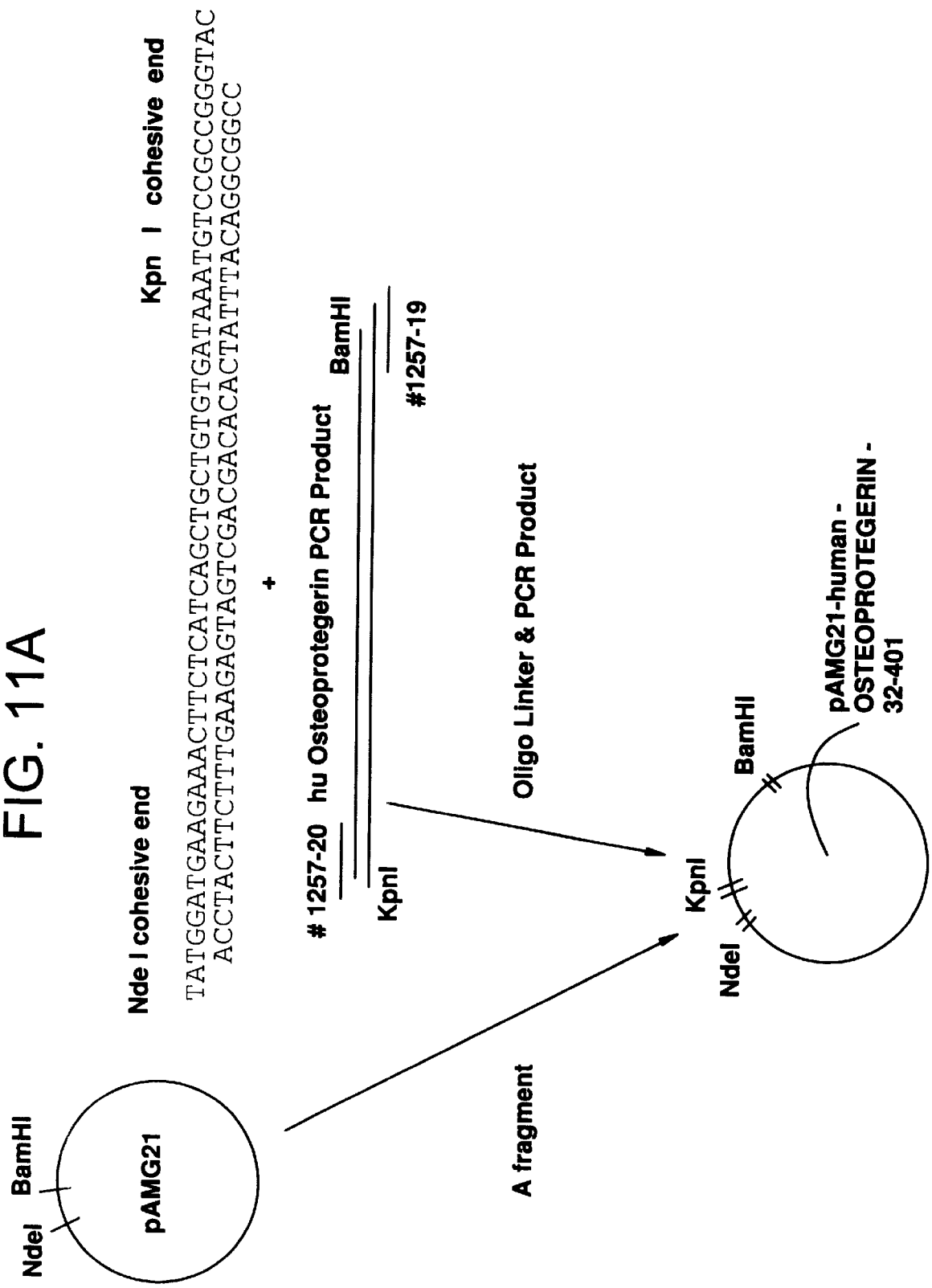
FIG. 11. Expression of human Osteoprotegerin in *E. coli*. A. Construction of a bacterial expression vector. The LORF of the human Osteoprotegerin gene was amplified by PCR, then joined to a oligonucleotide linker fragment (SEQ ID NO: 38), and ligated into pAMG21 vector DNA. The resulting vector is capable of expressing osteoprotegerin residues 32–401 linked to a N-terminal methionine residue. B SDS-PAGE analysis of uninduced and induced bacterial harboring the pAMG21-human Osteoprotegerin –32–401 plasmid. Lane 1, MW standards; lane 2, uninduced bacteria; lane 3, 30° C. induction; lane 4, 37° C. induction; lane 5, whole cell lysate from 37° C. induction; lane 6, soluble fraction of whole cell lysate; lane 7, insoluble fraction of whole cell lysate; lane 8, purified inclusion bodies obtained from whole cell lysate.
Figure 11B:
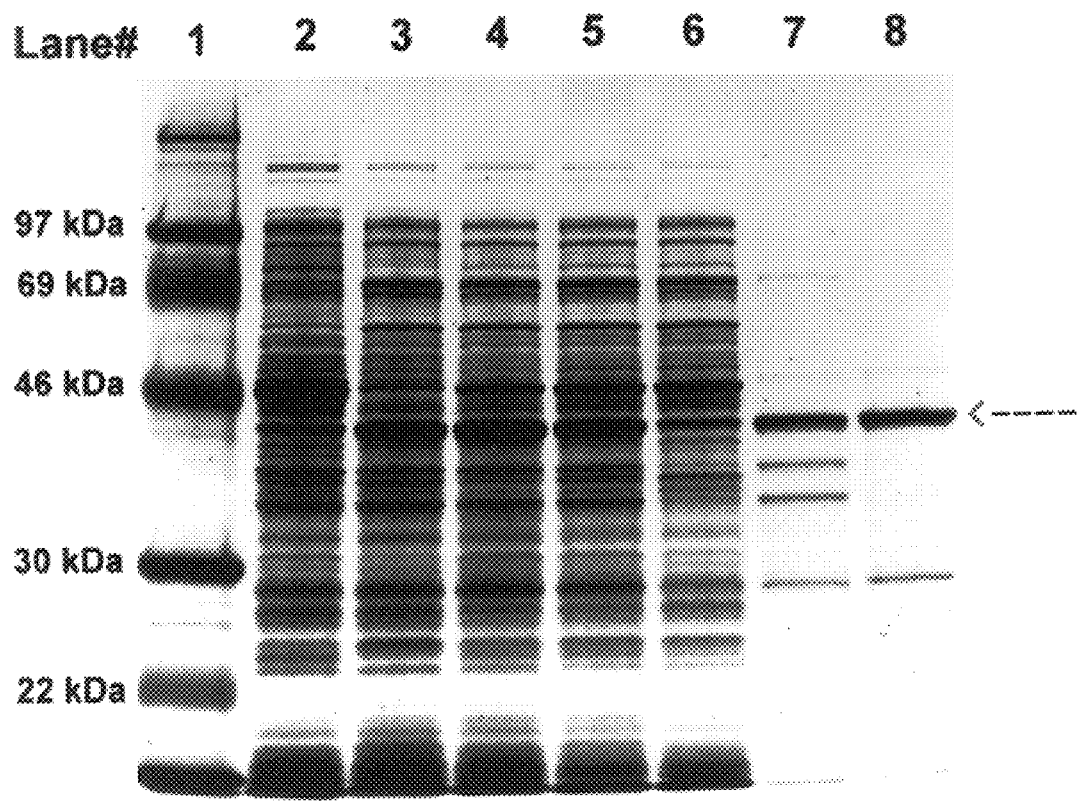

A novel member of the tumor necrosis factor receptor superfamily was identified as an expressed sequence tag (EST) isolated from a fetal rat intestinal cDNA library The structures of the full-length rat cDNA clones and the corresponding mouse and human cDNA clones were determined as described in Examples 1 and 6. The rat, mouse and human genes are shown in FIGS. 2A, 9A and 9B, respectively. All three sequences showed strong similarity to the extraceullular domains of TNFR family members. None of the full-length cDNA clones isolated encoded transmembrane and cytoplasmic domains that would be expected for membrane-bound receptors, suggesting that these cDNAs encode soluble, secreted proteins rather than cell surface receptors. A portion of the human genes spanning nucleotides 1200–1353 shown in FIG. 9B was deposited in the Genebank database on November 22, 1995 under accession no. 17188769.

The tissue distribution of the rat and human MRNA was determined as described in Example 2. In rat, MRNA expression was detected in kidney, liver, placenta and heart with the highest expression in the kidney. Expression in skeletal muscle and pancreas was also detected. In humans, expression was detected in the same tissues along with lymph node, thymus, spleen and appendix.

The rat cDNA was expressed in transgenic mice (Example 3) using the liver-specific ApoE promoter expression system. Analysis of expressors showed a marked increase in bone density, particularly in long bones (femurs), vertebrae and flat bones (pelvis). Histological analysis of stained sections of bone showed severe osteopetrosis (see Example 4) indicating a marked imbalance between bone formation and resorption which has led to a marked accumulation of bone and cartilage. A decrease in the number of trabecular osteoclasts in the bones of Osteoprotegerin expressor animals indicate that a significant portion of the activity of the TNFR- related protein may be to prevent bone resorption, a process mediated by osteoclasts. In view of the activity in transgenic expressors, the TNFR-related proteins described herein are termed osteoprotegerins.

Using the rat cDNA sequence, mouse and human cDNA clones were isolated (Example 5). Expression of mouse Osteoprotegerin in 293 cells and human osteoprotegerin in E. coli is described in Examples 6 and 7. Mouse Osteoprotectin was produced as an Fc fusion which was purified by Protein A affinity chromatography.

Osteoprotegerin may be important in regulating bone resorption. The protein appears to act as a soluble receptor of the TNF family and may prevent a receptor-ligand interaction involved in the osteolytic pathway. One aspect of the regulation appears to be a reduction in the number of osteoclasts.

Nucleic Acids

The invention provides for an isolated nucleic acid encoding a polypeptide having at least one of the biological activities of osteoprotegerin. As described herein, the biological activities of Osteoprotegerin include, but are not limited to, any activity involving bone metabolism and in particular, include increasing bone density. The nucleic acids of the invention are selected from the following:

a) the nucleic acid sequences as shown in FIGS. 2B, 9A and 9B or complementary strands thereof;

b) the nucleic acids which hybridize under stringent conditions with the polypeptide-encoding region in FIGS. 2B, 9A and 9B; and c) nucleic acids which hybridize under stringent conditions with nucleotides 148 through 337 inclusive as shown in FIG. 2B.

d) the nucleic acid sequences which are degenerate to the sequences in (a) and (b).

The invention provides for nucleic acids which encode rat, mouse and human Osteoprotegerin as well as nucleic acid sequences hybridizing thereto which encode a polypeptide having at least one of the biological activities of Osteoprotegerin. Also provides for nucleic acids which hybridize to a rat osteoprotegerin EST encompassing nucleotides 148–337 as shown in FIG. 2B. The conditions for hybridization are generally of high stringency such as 5xSSC, 50% formamide and 42° C. described in Example 1 of the specification. Equivalent stringency to these conditions may be readily obtained by adjusting salt and organic solvent concentrations and temperature. The nucleic acids in (b) encompass sequences encoding Osteoprotegerin-related polypeptides which do not undergo detectable hybridization with other known members of-the TNF receptor superfamily. In a preferred embodiment, the nucleic acids are as shown in FIGS. 2A, 9A and 9B.

DNA encoding rat osteoprotegerin was provided in plasmid pMO-B1.1 deposited with the American Type Culture Collection, 10801 University Blvd., Manassa, Va 20110-2209 on Dec. 27, 1995 under ATCC accession no. 69970. DNA encoding mouse Osteoprotegerin was provided in plasmid pRcCMV-murine Osteoprotegerin deposited with the American Type Culture Collection, 10801 University Blvd., Manassa, Va 20110-2209 on Dec. 27, 1995 under accession no. 69971. DNA encoding human Osteoprotegerin was provided in plasmid pRcCMV—human Osteoprotegerin deposited with the American Type Culture Collection, 10801 University Blvd., Manassa, Va 20110-2209 on Dec. 27, 1995 under accession no. 69969. Further, the nucleic acids of the invention will hybridize under stringent conditions to the DNA inserts of ATCC accession nos. 69969, 69970, and 69971 have at least one of the biological activities of osteoprotegerin.

Also provided by the invention are derivatives of the nucleic acid sequences as shown in FIGS. 2A, 9A and 9B. As used herein, derivatives include nucleic acid sequences having addition, substitution insertion or deletion of one or more residues such that the resulting sequences encode polypeptides having one or more amino acid residues which have been added, deleted, inserted or substituted and the resulting polypeptide has the activity of Osteoprotegerin. The nucleic acid. derivatives may be naturally occurring, such as by splice variation or polymorphism, or may be constructed using site-directed mutagenesis techniques available to the skilled worker. It is anticipated that nucleic acid derivatives will encode amino acid changes in regions of the molecule which are least likely to disrupt biological activity. Other derivatives include a nucleic acid encoding a membrane-bound form of Osteoprotegerin having an extracellular domain as shown in FIGS. 2B, 9A and 9B along with transmembrane and cytoplasmic domains.

Examples of the nucleic acids of the invention include cDNA, genomic DNA, synthetic DNA and RNA. cDNA is obtained from libraries prepared from mRNA isolated from various tissues expressing Osteoprotegerin. In humans, tissue sources for Osteoprotegerin include kidney, liver, placenta and heart. Genomic DNA encoding Osteoprotegerin is obtained from genomic libraries which are commercially available from a variety of species. Synthetic DNA is obtained by chemical synthesis of overlapping oligonucleotide fragments followed by assembly of the fragments to reconstitute part or all of the coding region and flanking sequences (see U.S. Pat. No. 4,695,623 describing the chemical synthesis of interferon genes). RNA is obtained most easily by procaryotic expression vectors which direct high-level synthesis of mRNA, such as vectors using T7 promoters and RNA polymerase.

Nucleic acid sequences of the invention are used for the detection of Osteoprotegerin sequences in biological samples in order to determine which cells and tissues are expressing Osteoprotegerin mRNA. The sequences may also be used to screen cDNA and genomic libraries for sequences related to Osteoprotegerin. Such screening is well within the capabilities of one skilled in the art using appropriate hybridization conditions to detect homologus sequences. The nucleic acids are also useful for modulating the expression of Osteoprotegerin levels by anti-sense therapy or gene therapy. The nucleic acids are also used for the development of transgenic animals which may be used for the production of the polypeptide and for the study of biological activity (see Example 3).

Vectors and Host Cells

Expression vectors containing nucleic acid sequences encoding Osteoprotegerin, host cells transformed with said vectors and methods for the production of Osteoprotegerin are also provided by the invention. An overview of expression of recombinant proteins is found in *Methods of Enzymology* v. 185 (Goeddel, D. V. ed.) Academic Press (1990).

Host cells for the production of Osteoprotegerin include procaryotic host cells, such as *E. coli,* yeast, plant, insect and mammalian host cells. *E. coli* strains such as HB101 or JM101 are suitable for expression. Preferred mammalian host cells include COS, CHOd-, 293, CV-1, 3T3, baby hamster kidney (BHK) cells and others. Mammalian host cells are preferred when post-translational modifications, such as glycosylation and polypeptide processing, are important for Osteoprotegerin activity. Mammalian expression allows for the production of secreted polypeptides which may be recovered from the growth medium.

Vectors for the expression of Osteoprotegerin contain at a minimum sequences required for vector propagation and for expression of the cloned insert. These sequences include a replication origin, selection marker, promoter, ribosome binding site, enhancer sequences, RNA splice sites and transcription termination site. Vectors suitable for expression in the aforementioned host cells are readily available and the nucleic acids of the invention are inserted into the vectors using standard recombinant DNA techniques. Vectors for tissue-specific expression of osteoprotegerin are also included. Such vectors include promoters which function specifically in liver, kidney or other organs for production in mice, and viral vectors for the expression of Osteoprotegerin in targeted human cells.

Using an appropriate host-vector system, Osteoprotegerin is produced recombinantly by culturing a host cell transformed with an expression vector containing nucleic acid sequences encoding Osteoprotegerin under conditions such that Osteoprotegerin is produced, and isolating the product of expression. Osteoprotegerin is produced in the supernatant of transfected mammalian cells or in inclusion bodies of transformed bacterial host cells. Osteoprotegerin so produced may be purified by procedures known to one skilled in the art as described below. The expression of Osteoprotegerin in mammalian and bacterial host systems is described in Example 6 and 7. It is anticipated that the specific plasmids and host cells described are for illustrative purpose and that other available plasmids and host cells could also be used to express the polypeptides.

The invention also provides for expression of Osteoprotegerin from endogenous nucleic acids by in vivo or ex vivo recombination events to allow modulation of Osteoprotegerin from the host chromosome.

Polypeptides

The invention provides for Osteoprotegerin, a novel member of the TNF receptor superfamily, having an activity associated with bone metabolism and in particular having the activity of inhibiting bone resorption thereby increasing bone density. Osteoprotegerin refers to a polypeptide having an amino acid sequence of mouse, rat or human Osteoprotegerin or a derivative thereof having at least one of the biological activities of Osteoprotegerin. The amino acid sequences of rat, mouse and human osteoprotegerin are shown in FIGS. 2A, 9A and 9B respectively. A derivative of Osteoprotegerin refers to a polypeptide having an addition, deletion, insertion or substitution of one or more amino acids such that the resulting polypeptide has at least one of the biological activities of Osteoprotegerin. The biological activities of Osteoprotegerin include, but are not limited to, activities involving bone metabolism. Preferably, the polypeptides will have the amino terminal leader sequence of 21 amino acids removed.

Osteoprotegerin polypeptides encompassed by the invention include rat [1–401], rat [22–180], rat [22–401], rat [22–401]-Fc fusion, rat [1–180]-Fc fusion, mouse [1–401], mouse [1–180], mouse [22–401], human [1–401], mouse [22–180], human [22–401], human [22–180], human [1–180], human [22–180]-Fc fusion and human met-32–401. Amino acid numbering is as shown in SEQ ID NO: 2 (rat), SEQ ID NO: 4 (mouse) and SEQ ID NO: 6 (human). Also encompassed are polypeptide derivatives having deletions or carboxy-terminal truncations of part or all of amino acids residues 180–401 of Osteoprotegerin; one or more amino acid changes in residues 180–401; deletion of part or all of a cysteine-rich domain of Osteoprotegerin, in particular deletion of the distal (carboxy-terminal) cysteine-rich domain; and one or more amino acid changes in a cysteine-rich domain, in particular in the distal (carboxy-terminal) cysteine-rich domain.

Modifications of Osteoprotegerin polypeptides are encompassed by the invention and include post-translational modifications (e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides may also be modified with a detectable label, such as an enzymatic, fluorescent, isotopic or affinity label to allow for detection and isolation of the protein.

Further modifications of Osteoprotegerin include chimeric proteins wherein Osteoprotegerin is fused to a heterologous amino acid sequence. The heterologous sequence may be any sequence which allows the resulting fusion protein to retain the activity of Osteoprotegerin. The heterologous sequences include for example, immunoglobulin fusions, such as Fc fusions, which may aid in purification of the protein.

The polypeptides of the invention are isolated and purified from other polypeptides present in tissues, cell lines and transformed host cells expressing Osteoprotegerin, or purified from components in cell cultures containing the secreted protein. In one embodiment, the polypeptide is free from association with other human proteins, such as the expression product of a bacterial host cell.

Also provided by the invention are chemically modified derivatives of osteoprotegerin which may provide additional advantages such as increasing stability and circulating time of the polypeptide, or decreasing immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

A method for the purification of Osteoprotegerin from natural sources and from transfected host cells is also included. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-Osteoprotegerin antibody or biotin-streptavidin affinity complex and the like.

Antibodies

Also encompassed by the invention are antibodies specifically binding to Osteoprotegerin. Antigens for the generation of antibodies may be full- length polypeptides or peptides spanning a portion of the Osteoprotegerin sequence. Immunological procedures for the generation of polyclonal or monoclonal antibodies reactive with Osteoprotegerin are known to one skilled in the art (see, for example, Harlow and Lane Antibodies: *A Laboratory Manual* Cold Spring Harbor Laboratory Press, Cold Spring Harbor N. Y. (1988)). Antibodies so produced are characterized for binding specificity and epitope recognition using standard enzyme-linked immunosorbent assays. Antibodies also include chimeric antibodies having variable and constant domain regions derived from different species. In one embodiment, the chimeric antibodies are humanized antibodies having murine variable domains and human constant domains. Also encompassed are complementary determining regions grafted to a human framework (so-called CDR-grafted antibodies). Chimeric and CDR-grafted antibodies are made by recombinant methods known to one skilled in the art. Also encompassed are human antibodies made in mice.

Anti-osteoprotegerin antibodies of the invention may be used as an affinity reagent to purify Osteoprotegerin from biological samples. In one method, the antibody is immobilized on CnBr-activated Sepharose and a column of antibody-Sepharose conjugate is used to remove Osteoprotegerin from liquid samples. Antibodies are also used as diagnostic reagents to detect and quantitate Osteoprotegerin in biological samples by methods described below.

Pharmaceutical Compositions

The invention also provides for pharmaceutical compositions comprising a therapeutically effective amount of the polypeptide of the invention together with a pharmaceutically acceptable diluent, carrier, solubilizer, emulsifier, preservative and/or adjuvant. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Also encompassed are compositions comprising Osteoprotegerin modified with water soluble polymers to increase solubility or stability. Compositions may also comprise incorporation of Osteoprotegerin into liposomes, microemulsions, micelles or vesicles for controlled delivery over an extended period of time. Selection of a particular composition will depend upon a number of factors, including the condition being treated, the route of administration and the pharmacokinetic parameters desired. A more extensive survey of component suitable for pharmaceutical compositions is found in *Reminaton's Pharmaceutical Sciences*, 18th ed. A. R. Gennaro, ed. Mack, Easton, PA (1980).

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the Osteoprotegerin coding region to cells and tissues as part of an anti-sense or gene therapy regimen.

Methods of Treatment

Bone tissue provides support for the body and consists of mineral (largely-calcium and phosphorous), a matrix of collagenous and noncollagenous proteins, and cells. Three types of cells found in bone, osteocytes, osteoblasts and osteoclasts, are involved in the dynamic process by which bone is continually formed and resorbed. Osteoblasts promote formation of bone tissue whereas osteoclasts are associated with resorption. Resorption, or the dissolution of bone matrix and mineral, is a fast and efficient process compared to bone formation and can release large amounts of mineral from bone. Osteoclasts are involved in the regulation of the normal remodeling of skeletal tissue and in resorption induced by hormones. For instance, resorption is stimulated by the secretion of parathyroid hormone in response to decreasing concentrations of calcium ion in extracellular fluids. In contrast, inhibition of resorption is the principal function of calcitonin. In addition, metabolites of vitamin D alter the responsiveness of bone to parathyroid hormone and calcitonin.

After skeletal maturity, the amount of bone in the skeleton reflects the balance (or imbalance) of bone formation and bone resorption. Peak bone mass occurs after skeletal maturity prior to the fourth decade. Between the fourth and fifth decades, the equilibrium shifts and bone resorption dominates. The inevitable decrease in bone mass with advancing years starts earlier in females than males and is distinctly accelerated after menopause in some females (principally those of Caucasian and Asian descent).

Osteopenia is a condition relating generally to any decrease in bone mass to below normal levels. Such a condition may arise from a decrease in the rate of bone synthesis or an increase in the rate of bone destruction or both. The most common form of osteopenia is primary osteoporosis, also referred to as postmenopausal and senile osteoporosis. This form of osteoporosis is a consequence of the universal loss of bone with age and is usually a result of increase in bone resorption with a normal rate of bone formation. About 25 to 30 percent of all white females in the United States develop symptomatic osteoporosis. A direct relationship exists between osteoporosis and the incidence of hip, femoral, neck and inter-trochanteric fracture in women 45 years and older. Elderly males develop symptomatic osteoporosis between the ages of 50 and 70, but the disease primarily affects females.

The cause of postmenopausal and senile osteoporosis is unknown. Several factors have been identified which may contribute to the condition. They include alteration in hormone levels accompanying aging and inadequate calcium consumption attributed to decreased intestinal absorption of calcium and other minerals. Treatments have usually included hormone therapy or dietary supplements in an attempt to retard the process. To date, however, an effective treatment for bone loss does not exist.

The invention provides for a method of treating a bone disorder using a therapeutically effective amount of Osteoprotegerin. The bone disorder may be any disorder characterized by a net bone loss (osteopenia or osteolysis). In general, treatment with Osteoprotegerin is anticipated when it is necessary to suppress the rate of bone resorption. Thus treatment may be done to reduce the rate of bone resorption where the resorption rate is above normal or to reduce bone resorption to below normal levels in order to compensate for below normal levels of bone formation.

Conditions which are treatable with osteoprotegerin include the following:

Osteoporosis, such as primary osteoporosis, endocrine osteoporosis (hyperthyroidism, hyperparathryoidism, Cushing's syndrome, and acromegaly), hereditary and congenital forms of osteoporosis (osteogenesis imperfecta, homocystinuria, Menkes' syndrome, and Riley-Day syndrome) and osteoporosis due to immobilization of extremities.

Paget's disease of bone (osteitis deformans) in adults and juveniles.

Osteomyelitis, or an infectious lesion in bone, leading to bone loss.

Hypercalcemia resulting from solid tumors (breast, lung and kidney) and hematologic malignacies (multiple myeloma, lymphoma and leukemia), idiopathic hypercalcemia, and hypercalcemia associated with hyperthryoidism and renal function disorders.

Osteopenia following surgery, induced by steroid administration, and associated with disorders of the small and large intestine and with chronic hepatic and renal diseases.

Osteonecrosis, or bone cell death, associated with traumatic injury or nontraumatic necrosis associated with Gaucher's disease, sickle cell anemia, systemic lupus erythematosus and other conditions.

Bone loss due to rheumatoid arthritis.

Periodontal bone loss.

Osteolytic metastasis.

It is understood that Osteoprotegerin may be used alone or in conjunction with other factors for the treatment of bone disorders. In one embodiment, osteoprotegerein is used in conjunction with a therapeutically effective amount of a factor which stimulates bone formation. Such factors include but are not limited to the bone morphogenic factors designated BMP-1 through BMP-12, transforming growth factor-β (TGF-β) and TGF-β family members, interleukin-1 inhibitors, TNFβ inhibitors, parathyroid hormone and analogs thereof, parathyroid related protein and analogs thereof, E series prostaglandins, bisphosphonates (such as alendronate and others), and bone-enhancing minerals such as fluoride and calcium.

The following examples are offered to more fully illustrate the invention, but are not construed as limiting the scope thereof.

EXAMPLE 1

Identification and Isolation of the Rat Osteoprotegerin cDNA

Materials and method for cDNA closing and analysis are described in Maniatis et al. Molecular Cloning, 2d ed., CHSL Press (1989). A cDNA library was constructed using mRNA isolated from embryonic d20 intestine for EST analysis (Adams et al. Science 252: 1651–1656 (1991)). Rat embryos were dissected, and the entire developing small and large intestine removed and washed in PBS. Total cell RNA was purified by acid guanidinium thiocyanate-phenolchloroform extraction (Chomczynski and Sacchi Anal. Biochem. 162. 156–159, (1987)). The poly (A+) mRNA fraction was obtained from the total RNA preparation by adsorption to, and elution from, Dynabeads Oligo (dT)25 (Dynal Corp) using the manufacturer's recommended procedures. A random primed CDNA library was prepared using the Superscript Plasmid System (Gibco BRL, Gaithersburg, Md). The random cDNA primer containing an internal Not I restriction site was used to initiate first strand synthesis and had the following sequence:

(SEQ ID NO:7)
5'-AAAGGAAGGAAAAAAGCGGCCGCTACANNNNNNNNT-3'
Not I

For the first strand synthesis three separate reactions were assembled that contained 2.5 ug of poly(A) RNA and 120 ng, 360 ng or 1,080 ng of random primer. After second strand synthesis, the reaction products were separately extracted with a mixture of phenol:choroform:isoamyl alcohol (25:24:1 ratio), and then ethanol precipitated. The double strand (ds) cDNA products of the three reactions were combined and ligated to the following ds oligonucleotide adapter:

| 5'-TCGACCCACGCGTCCG-3' | (SEQ ID NO: 8) |
| 3'-GGGTGCGCAGGCp-5' | (SEQ ID NO: 9) |

After ligation the cDNA was digested to completion with Not I, extracted with phenol:chloroform:isoamyl (25:24:1) alcohol and ethanol precipitated. The resuspended cDNA was then size fractionated by gel filtration using premade columns provided with the Superscript Plasmid System (Gibco BRL, Gaithersburg, Md.) as recommended by the manufacturer.

The two fractions containing the largest CDNA products were pooled, ethanol precipitated and then directionally ligated into Not I and Sal I digested PMOB vector DNA (Strathmann et al, 1991). The ligated cDNA was introduced into competent ElectroMAX DH10B *E. coli* (Gibco BRL, Gaithersburg, Md.) by electroporation. For automated sequence analysis approximately 10,000 transformants were plated on 20 cm×20 cm agar plates containing ampicillin supplemented LB nutrient media. The colonies that arose were picked and arrayed onto 96 well microtiter plates containing 200 μl of L-broth, 7.5% glycerol, and 50 μg/ml ampicillin. The cultures were grown overnight at 37° C., a duplicate set of microtiter plates were made using a sterile 96 pin replicating tool, then both sets were stored at −80° C. for further analysis. For full-length cDNA cloning approximately one million transformants were plated on 96 bacterial ampicillin plates containing about 10,000 clones each. The plasmid DNA from each pool was separately isolated using the Qiagen Plasmid Maxi Kit (Qiagen Corp.,Germany) and arrayed into 96 microtiter plates for PCR analyses.

To sequence random fetal rat intestine cDNA clones, glycerol stocks were thawed, and small aliquots diluted 1:25 in distilled. Approximately 3.0 ul of diluted bacterial cultures were added to PCR reaction mixture (Boehringer-Mannheim) containing the following oligonucleotides:

| 5'-TGTAAAACGACGGCCAGT-3' | (SEQ ID NO: 10) |
| 5'-CAGGAAACAGCTATGACC-3' | (SEQ ID NO: 11) |

The reactions were incubated in a thermocycler (Perkin-Elmer 9600) with the following cycle conditions: 94 C for 2 minutes; 30 cycles of 94 C for 5 seconds, 50 C for 5 seconds, and 72 C for 3 minutes.; 72 C for 4 minutes. After incubation in the thermocycler, the reactions were diluted with 2.0 mL of water. The amplified DNA fragments were further purified using Centricon columns (Princeton Separations) using the manufacturer's recommended procedures. The PCR reaction products were sequenced on an Applied Biosystems 373A automated DNA sequencer using T3 primer (oligonucleotide 353-23;

5'-CAATTAACCCTCACTAAAGG-3') (SEQ ID NO: 12) Taq dye-terminator reactions (Applied Biosystems) following the manufacturer's recommended procedures.

The resulting 5' nucleotide sequence obtained from randomly picked cDNA clones translated and then compared to the existing database of known protein sequences using a modified version of the FASTA program (Pearson et al. Meth. Enzymol. 18, (1990)). Translated sequences were also analysed for the presence of a specific cysteine-rich protein motif found in all known members of the tumor necrosis factor receptor (TNFR) superfamily (Smith et al. Cell 76, 959–962 (1994)), using the sequence profile method of Gribskov et al. (PNAS USA 83, 4355–4359 (1987), as modified by Luethy et al. (Protein Science 3, 139–146 (1994)).

Using the FASTA and Profile search data, an EST, FRI-1 (Fetal Rat Intestine-1), was identified as a possible new member of the TNFR superfamily. FRI-1 contained an approximately 600 bp insert with a LORF of about 150 amino acids. The closest match in the database was the human type II TNFR (TNFR-2). The region compared showed an ~43% homology between TNFR-2 and FRI-1 over this 150 aa LORF. Profile analysis using the first and second cysteine-rich repeats of the TNFR superfamily yielded a Z score of ~8, indicating that the FRI-1 gene possibly encodes a new family member. To deduce the structure of the FRI-1 product, the fetal rat intestine cDNA library was screened for full length clones. The following oligonucleotides were derived from the original FRI-1 sequence:

5'-GCATTATGACCCAGAAACCGGAC-3'    (SEQ ID NO: 13)

5'-AGGTAGCGCCCTTCCTCACATTC-3'    (SEQ ID NO: 14)

These primers were used in PCR reactions to screen 96 pools of plasmid DNA, each pool containing plasmid DNA from 10,000 independent cDNA clones. Approximately 1 ug of plasmid pool DNA was amplified in a PCR reaction mixture (Boehringer-Mannheim) using a Perkin-Elmer 96 well thermal cycler with the following cycle conditions: 2 min at 94° c.,1 cycle; 15 sec at 94° c., then 45 sec at 65° c., 30 cycles; 7 min at 65° C., 1 cycle. PCR reaction products were analysed by gel electrophoresis. 13 out of 96 plasmid DNA pools gave rise to amplified DNA products with the expected relative molecular mass.

DNA from one positive pool was used to transform competent ElectroMAX DH10B *E. coli* (Gibco BRL, Gaithersburg, Md.) as described above. Approximately 40,000 transformants were plated onto sterile nitrocellulose filters (BA-85, Schleicher and Schuell), and then screened by colony hybridization using a $^{32}$p-dCTP labelled version of the PCR product obtained above.

Filters were prehybridized in 5×SSC, 50% deionized formamide, 5×Denhardt's solution, 0.5% SDS, and 100 ug/ml denatured salmon sperm DNA for 2–4 hours at 42° C.

Filters were then hybridized in 5X SSC, 50% deionized formamide, 2×Denhardt's solution, 0.1% SDS, 100 ug/ml denatured salmon sperm DNA, and ~5 ng/ml of labelled probe for ~18 hours at 42° C. The filters were then washed in 2×SSC for 10 min at RT, 1×SSC for 10 min at 55° C., and finally in 0.5×SSC for 10–15 min at 55° C. Hybridizing clones were detected following autoradiography, and then replated onto nitrocellulose filters for secondary screening. Upon secondary screening, a plasmid clone (pB1.1) was isolated, then amplified in L-broth media containing 100 ug/ml ampicillin and the plasmid DNA obtained. Both strands of the 2.4 kb pB1.1 insert were sequenced.

The pB1.1 insert sequence was used for a FASTA search of the public database to detect any existing sequence matches and/or similarities. No matches to any known genes or EST's were found, although there was an approximate 45% similarity to the human and mouse TNFR-2 genes. A methionine start codon is found at bp 124 of the nucleotide sequence, followed by a LORF encoding 401 aa residues that terminates at bp 1327. The 401 aa residue product is predicted to have a hydrophobic signal peptide of approximately 31 residues at its N-terminus, and 4 potential sites of N-linked glycosylation. No hydrophobic transmembrane spanning sequence was identified using the PepPlot program (Wisconsin GCG package, version 8.1). The deduced 401 aa sequence was then used to search the protein database. Again, there were no existing matches, although there appeared to be a strong similarity to many members of the TNFR superfamily, most notably the human and mouse TNFR-2. A sequence alignment of this novel protein with known members of the TNFR-superfamily was prepared using the Pileup program, and then modified by PrettyPlot (Wisconsin GCG package, version 8.1). This alignment shows a clear homology between the full length FRI-1 gene product and all other TNFR family members. The homologus region maps to the extracellular domain of TNFR family members, and corresponds to the three or four cysteine-rich repeats found in the ligand binding domain of these proteins. This suggested that the FRI-1 gene encoded a novel TNFR family member. Since no transmembrane spanning region was detected we predicted that this may be a secreted receptor, similar to TNFR-1 derived soluble receptors (Kohno et al. PNAS USA 87, 8331-8335 (1990)). Due to the apparent biological activity of the FRI-1 gene (vide infra), the product was named Osteoprotegerin.

EXAMPLE 2

Osteoprotegerin mRNA Expression Patterns in Tissues

Multiple human tissue northern blots (Clonetech) were probed with a 32P-dCTP labelled FRI-1 PCR product to detect the size of the human transcript and to determine patterns of expression. Northern blots were prehybridized in 5×SSPE, 50% formamide, 5×Denhardt's solution, 0.5% SDS, and 100 ug/ml denatured salmon sperm DNA for 2–4 hr at 42° C. The blots were then hybridized in 5×SSPE, 50% formamide, 2×Denhardt's solution, 0.1% SDS, 100 ug/ml denatured salmon sperm DNA, and 5 ng/ml labelled probe for 18–24 hr at 42° C. The blots were then washed in 2×SSC for 10 min at RT, 1×SSC for 10 min at 50° C., then in 0.5×SSC for 10–15 min.

Using a probe derived from the rat gene, a predominant mRNA species with a relative molecular mass of about 2.4 kb is detected in several tissues, including kidney, liver, placenta, and heart. Highest levels are detected in the kidney. A large MRNA species of Mr 4.5 and 7.5 kb was detected in skeletal muscle and pancreas. In human fetal tissue, kidney was found to express relatively high levels of the 2.4 kb mRNA. Using a human probe (vide infra), only the 2.4 kb transcript is detected in these same tissues. In addition, relatively high levels of the 2.4 kb transcript was detected in the lymph node, thymus, spleen and appendix. The size of the transcript detected by both the rat and human Osteoprotegerin gene is almost identical to the length of the rat pB1.1 FRI-1 insert, suggesting it was a full length CDNA clone.

EXAMPLE 3

Systemic delivery of Osteoprotegerin in Transgenic Mice

The rat Osteoprotegerin clone pB1.1 was used as template to PCR amplify the coding region for subcloning into an ApoE-liver specific expression vector (Simonet et al. J. Clin. Invest. 94, 1310–1319 (1994), and PCT Application No. US94/11675 and co-owned U.S. Ser. No. 08/221,767. The following 5' and 3' oligonucleotide primers were used for PCR amplification, respectively:

5'-GACTAGTCCCACAATGAACAAGTG
    GCTGTG-3' (SEQ ID NO: 15)

5'-ATAAGAATGCGGCCGCTAAACTATGAAA-
    CAGCCCAGTGACCATTC-3' (SEQ ID NO: 16)

The PCR reaction mixture (Boehringer-Mannheim) was treated as follows: 94° C. for 1 minute, 1 cycle; 94° C. for 20 sec, 62° C. for 30 sec, and 74 C for 1 minute, 25 cycles. Following amplification, the samples were purified over Qiagen PCR columns and digested overnight with SpeI and NotI restriction enzymes. The digested products were extracted and precipitated and subcloned into the ApoE promoter expression vector. Prior to microinjecting the resulting clone, HE-Osteoprotegerin, it was sequenced to ensure it was mutation-free.

The HE-Osteoprotegerin plasmid was purified through two rounds of CsCl density gradient centrifugation. The purified plasmid DNA was digested with XhoI and Ase I, and the 3.6 kb transgene insert was purified by gel electrophoresis. The purified fragment was diluted to a stock injection solution of 1 ug/ml in 5 mM Tris, pH 7.4, 0.2 mM EDTA. Single-cell embryos from BDF1xBDF1-bred mice were injected essentially as described (Brinster et al., PNAS USA 21, 4338 (1985)), except that injection needles were beveled and siliconized before use. Embryos were cultured overnight in a $CO_2$ incubator and 15 to 20 2-cell embryos were transferred to the oviducts of pseudopregnant CD1 female mice.

Following term pregnancy, 49 offspring were obtained from implantation of microinjected embryos.

The offspring were screened by PCR amplification of the integrated transgene in genomic DNA samples. The target region for amplification was a 369 bp region of the human Apo E intron which was included in the expression vector. The oligos used for PCR amplification were:

5'-GCC TCT AGA AAG AGC TGG GAC-3' (SEQ ID NO: 17)

5'-CGC CGT GTT CCA TTT ATG AGC-3' (SEQ ID NO: 18)

The conditions for PCR were: 94° C. for 2 minute, 1 cycle; 94° C. for 1 min, 63° C. for 20 sec, and 72° C. for 30 sec, 30 cycles. Of the 49 original offspring, 9 were identified as PCR positive transgenic founders.

At 8–10 weeks of age, five transgenic founders (2, 11, 16, 17, and 28) and five controls (1, 12, 15, 18, and 30) were sacrificed for necropsy and pathological analysis. Liver was isolated from the remaining 4 founders by partial hepatectomy. For partial hepatectomy, the mice were anesthetized and a lobe of liver was surgically removed. Total cellular RNA was isolated from livers of all transgenic founders, and 5 negative control littermates as described (McDonald et al. Meth. Enzymol. 1, 219 (1987)). Northern blot analysis was performed on these samples to assess the level of transgene expression. Approximately 10 ug of total RNA from each animal liver was resolved by electrophoresis denaturing gels (Ogden et al. Meth. Enzymol 15, 61 (1987)), then transferred to HYBOND-N nylon membrane (Amersham), and probed with 32P dCTP-labelled pB1.1 insert DNA. Hybridization was performed overnight at 42° C. in 50% Formamide, 5xSSPE, 0.5% SDS, 5xDenhardt's solution, 100 ug/ml denatured salmon sperm DNA and $2-4 \times 10^6$ cpm of labeled probe/ml of hybridization buffer. Following hybridization, blots were washed twice in 2xSSC, 0.1% SDS at room temperature for 5 min each, and then twice in 0.1xSSC, 0.1% SDS at 55° C. for 5–10 min each. Expression of the transgene in founder and control littermates was determined following autoradiography.

The northern blot data indicate that 7 of the transgenic founders express detectable levels of the transgene mRNA (animal #'s 2,11,16,17,22,33,and 45).

The negative control mice and one of the founders (#28) expressed no transgene-related mRNA. Since Osteoprotegerin is predicted to be a secreted protein, overexpression of transgene mRNA should be a proxy for the level of systemically delivered gene product. Of the PCR and northern blot positive mice, animal 2, 17 and 22 expressed the highest levels of transgene mRNA, and may show more extensive biological effects on host cells and tissues.

EXAMPLE 4

Biological Activity of Osteoprotegerin

Five of the transgenic mice (animals 2,11,16,17 and 28) and 5 control littermates (animals 1,12,15,18, and 30) were sacrificed for necropsy and pathological analysis using the following procedures: Prior to euthanasia, all animals had their identification numbers verified, then were weighed, anesthetized and blood drawn. The blood was saved as both serum and whole blood for a complete serum chemistry and hematology panel. Radiography was performed just after terminal anesthesia by lethal C02 inhalation, and prior to the gross dissection. Following this, tissues were removed and fixed in 10% buffered Zn-Formalin for histological examination. The tissues collected included the liver, spleen, pancreas, stomach, duodenum, ileum, colon, kidney, reproductive organs, skin and mammary glands, bone, brain, heart, lung, thymus, trachea, eosphagus, thyroid, jejunem, cecum, rectum, adrenals, urinary bladder, and skeletal muscle. Prior to fixation the whole organ weights were determined for the liver, stomach, kidney, adrenals, spleen, and thymus. After fixation the tissues were processed into paraffin blocks, and 3 um sections were obtained. Bone tissue was decalcified using a formic acid solution, and all sections were stained with hematoxylin and eosin. In addition, staining with Gomori's reticulin and Masson's trichrome were performed on certain tissues. Enzyme histochemistry was performed to determine the expression of tartrate resistant acid phosphatase (TRAP), an enyzme highly expressed by osteoclasts, multinucleated bone-resorbing cells of monocyte-macrophage lineage. Immunohistochemistry for BrdU and F480 monocyte-macrophage surface antigen was also performed to detect replicating cells and cells of the monocyte-macrophage lineage, respectively. To detect F480 surface antigen expression, formalin fixed, paraffin embedded 4 $\mu$m sections were deparaffinized and hydrated to deionized water. The sections were quenched with 3% hydrogen peroxide, blocked with Protein Block (Lipshaw, Pittsburgh, PA), and incubated in rat monoclonal anti-mouse F480 (Harlan, Indianapolis, Ind.). This antibody was detected by biotinylated rabbit anti-rat immunoglobulins, peroxidase conjugated strepavidin (BioGenex San Ramon, Calif.) with DAB as chromagen (BioTek, Santa Barbara, Calif.). Sections were counterstained with hematoxylin.

Upon gross dissection and observation of visceral tissues, no abnormalities were found in the transgene expressors or control littermates. Analysis of organ weight indicate that spleen size increased by approximately 38% in the transgenic mice relative to controls. There was a slight enlargement of platelet size and increased circulating unstained cells in the transgene expressors. There was a marginal decrease in platelet levels in the transgene expressors. In addition, the serum uric acid, urea nitrogen, and alkaline phosphatase levels all trended lower in the transgene expressors. The expressors were found to have increased radiodensity of the skeleton, including long bones (femurs), vertebrae, and flat bones (pelvis). The relative size of femurs in the expressors were not different from the the control mice.

Histological analysis of stained sections of bone from the Osteoprotegerin expressors show severe osteopetrosis with the presence of cartilage remnants from the primary spongiosa seen within bone trabeculae in the diaphysis of the femur. A clearly defined cortex was not identifiable in the sections of femur. In normal animals, the central diaphysis is filled with bone marrow. Sections of vertebra also show osteopetrotic changes implying that the Osteoprotegerin-induced skeletal changes were systemic. The residual bone marrow showed predominantly myeloid elements. Megakaryocytes were present. Reticulin stains showed no evidence for reticulin deposition. Immunohistochemistry for F480, a cell surface antigen expressed by cells of monocyte-macrophage derivation in the mouse, showed the presence of F480 positive cells in the marrow spaces. Focally, flattened F480 positive cells could be seen directly adjacent to trabecular bone surfaces.

The mesenchymal cells lining the bony trabeculae were flattened and appeared inactive. Based on H&E and TRAP stains, osteoclasts were rarely found on the trabecular bone surfaces in the Osteoprotegerin expressors. In contrast, osteoclasts and/or chondroclasts were seen in the region of the growth plate resorbing cartilage, but their numbers may be reduced compared to controls. Also, osteoclasts were present on the cortical surface of the metaphysis where modelling activity is usually robust. The predominant difference between the expressors and controls was the profound decrease in trabecular osteoclasts, both in the vertebrae and femurs. The extent of bone accumulation was directly correlated with the level of Osteoprotegerin transgene mRNA detected by northern blotting of total liver RNA.

The spleens from the Osteoprotegerin expressors had an increased amount of red pulp with the expansion due to increased hematopoiesis. All hematopoietic lineages are represented. F480 positive cells were present in both control and Osteoprotegerin expressors in the red pulp. Two of the expressors (2 and 17)had foci of extramedullary hematopoiesis within the liver and this is likely due to the osteopetrotic marrow.

There were no observable abnormalities in the thymus, lymph nodes, gastrointestinal tract, pancreato-hepatobiliary tract, respiratory tract, reproductive system, genito-urinary system, skin, nervous system, heart and aorta, breast, skeletal muscle and fat.

EXAMPLE 5

Isolation of Mouse and Human Osteoprotegerin cDNA

A cDNA clone corresponding to the 5' end of the mouse Osteoprotegerin mRNA was isolated from a mouse kidney CDNA library (Clontech) by PCR amplification. The oligo nucleotides were derived from the rat Osteoprotegerin CDNA sequence and are shown below:

| | |
|---|---|
| 5'-ATCAAAGGCAGGGCATACTTCCTG-3' | (SEQ ID NO: 19) |
| 5'-GTTGCACTCCTGTTTCACGGTCTG-3' | (SEQ ID NO: 20) |
| 5'-CAAGACACCTTGAAGGGCCTGATG-3' | (SEQ ID NO: 21) |
| 5'-TAACTTTTACAGAAGAGCATCAGC-3' | (SEQ ID NO: 22) |
| 5'-AGCGCGGCCGCATGAACAAGTGGCTGTGCTGCG-3' | (SEQ ID NO: 23) |
| 5'-AGCTCTAGAGAAACAGCCCAGTGACCATTCC-3' | (SEQ ID NO: 24) |

The partial and full-length CDNA products obtained in this process were sequenced. The full-length product was digested with Not I and Xba I, then directionally cloned into the plasmid vector pRcCMV (Invitrogen). The resulting plasmid was named pRcCMV-Mu-Osteoprotegerin. The nucleotide sequence of the cloned product was compared to the rat Osteoprotegerin cDNA sequence. Over the 1300 bp region spanning the Osteoprotegerin LORF, the rat and mouse DNA sequences are approximately 88% identical. The mouse cDNA sequence contained a 401 aa LORF, which was compared to the rat Osteoprotegerin protein sequence and found to be ~94% identical without gaps. This indicates that the mouse cDNA sequence isolated encodes the murine Osteoprotegerin protein, and that the sequence and structure has been highly conserved throughout evolution. The mouse Osteoprotegerin protein sequence contains an identical putative signal peptide at its N-terminus, and all 4 potential sites of N-linked glycosylation are conserved.

A partial human Osteoprotegerin CDNA was cloned from a human kidney CDNA library using the following rat-specific oligonucleotides:

| | |
|---|---|
| 5'-GTG AAG CTG TGC AAG AAC CTG ATG-3' | (SEQ ID NO: 255) |
| 5'-ATC AAA GGC AGG GCA TAC TTC CTG-3' | (SEQ ID NO: 26) |

This PCR product was sequenced and used to design primers for amplifying the 3' end of the human cDNA using a human osteoprotegerin genomic clone in lambda as template:

| | |
|---|---|
| 5'-TCCGTAAGAAACAGCCCAGTGACC-3' | (SEQ ID NO: 27) |
| 5'-CAGATCCTGAAGCTGCTCAGTTTG-3' | (SEQ ID NO: 28) |

The amplified PCR product was sequenced, and together with the 5' end sequence, was used to design 5' and 3' human-specific primers useful for amplifying the entire human Osteoprotegerin cDNA coding sequences:

| | |
|---|---|
| 5'-AGCGCGGCCGCGGGGACCACAATGAAC AAGTTG-3' | (SEQ ID NO: 29) |
| 5'-AGCTCTAGAATTGTGAGGAAACAGCTC AATGGC-3' | (SEQ ID NO: 30) |

The full-length human PCR product was sequenced, then directionally cloned into the plasmid vector pRcCMV (Invitrogen) using Not I and Xba I. The resulting plasmid was named pRcCMV-human Osteoprotegerin. The nucleotide sequence of the cloned product was compared to the rat and mouse Osteoprotegerin cDNA sequences. Over the 1300 bp region spanning the Osteoprotegerin LORF, the rat and mouse DNA sequences are approximately 78–88% identical to the human Osteoprotegerin cDNA. The human Osteoprotegerin cDNA sequence also contained a 401 aa LORF, and it was compared to the rat and mouse protein sequences. The predicted human Osteoprotegerin protein is approximatley 85% identical, and ~90% identical to the rat and mouse proteins, respectively. Sequence alignment of rat, mouse and human proteins show that they have been highly conserved during evolution. The human protein is predicted to have a N-terminal signal peptide, and 5 potential sites of N-linked glycosylation, 4 of which are conserved between the rat and mouse Osteoprotegerin proteins.

EXAMPLE 6

Production of Pecombinant Secreted Osteoprotegerin Protein in Mammalian Cells To determine if Osteoprotegerin is actually a secreted protein we expressed the mouse CDNA, fused to the human IgG1 Fc domain as a tag (Capon et al. Nature 337, 525-531 (1989)), in human 293 fibroblasts. The cloned mouse cDNA was amplified using the following two sets of primer pairs:

Pair 1

5'-CCTCTGAGCTCAAGCTTCCGAGGACCACAATGAACAAG-3' (SEQ ID NO: 31)

5'-CCTCTGCGGCCGCTAAGCAGCT-TATTTTCACGGATTGAACCTG-3' (SEQ ID NO: 32)

Pair 2

5'-CCTCTGAGCTCAAGCTTCCGAGGACCACAATGAACAAG-3' (SEQ ID NO: 33)

5'-CCTCTGCGGCCGCTGTTGCATTTCCTTT CTG-3' (SEQ ID NO: 34)

The first pair amplifies the entire Osteoprotegerin LORF, and creates a Not I restriction site which is compatable with the in-frame Not I site Fc fusion vector FcA3. FcA3 was prepared by engineering a Not 1 restriction site 5' to aspartic acid reside 216 of the human IgG1 Fc cDNA. This construct introduces a linker which encodes two irrelevant amino acids which span the junction between-the Osteoprotegerin protein and the IgG Fc region. This product, when linked to the Fc portion, would encode all 401 Osteoprotegerin residues directly followed by all 227 amino acid residues of the human IgG1 Fc region (Fl.Fc). The second primer pair amplifies the DNA sequences encoding the first 180 amino acid residues of Osteoprotegerin, which encompasses its putative ligand binding domain. As above, the 3' primer creates an artifical Not I restriction site which fuses the C-terminal truncated Osteoprotegerin LORF at position Threonine$_{180}$ directly to the IgG1 Fc domain (CT.Fc).

Both products were directionally cloned into the plasmid vector pCEP4 (Invitrogen). pCEP4 contains the Epstein-Barr virus origin of replication, and is capable of episomal replication in 293-EBNA-1 cells. The parent pCEP4, and pCEP4-Fl.Fc and pCEP4-CT.Fc vectors were lipofected into 293-EBNA-1 cells using the manufacturer's recommended methods. The transfected cells were then selected in 100 μg/ml hygromycin to select for vector expression, and the resulting drug-resistant mass cultures were grown to confluence. The cells were then cultured in serum-free media for 72 hr, and the conditioned media removed and analysed by SDS-PAGE. A silver staining of the polyacrylamide gel detects the major conditioned media proteins produced by the drug resistant 293 cultures. In the pCEP4-Fl.Fc and the pCEP4-CT.Fc conditioned media, unique band of the predicted size were abundantly secreted. The full-length Fc fusion protein accumulated to a high concentration, indicating that it may be stable. Both Fc fusion proteins were detected by anti-human IgG1 Fc antibodies (Pierce) on western blots, indicating that they are recombinant Osteoprotegerin products.

The full length Osteoprotegerin-Fc fusion protein was purified by Protein-A column chromatography (Pierce) using the manufacturers recommended procedures.

The protein was then subjected to N-terminal sequence analysis by automated Edman degradation as essentially described by Matsudaira et al. (J. Biol. Chem. 26, 10–35 (1987)). The following amino acid sequence was read after 19 cycles (SEQ ID NO: 35):

NH$_2$—E T L P P K Y L H Y D P E T G H Q L L—CO$_2$H

This sequence was identical to the predicted mouse Osteoprotegerin amino acid sequence beginning at amino acid residue 22, suggesting that the natural mammalian leader cleavage site is between amino acid residues $Q_{21}$-$E_{22}$, not between Y31-D32 as originally predicted. The expression experiments performed in 293- EBNA cells with pCEP4-Fl.Fc and pCEP4-CT.Fc demonstrate that Osteoprotegerin is a secreted protein, and may act systemically to bind its unidentified ligand.

EXAMPLE 7

Expression of Human Osteoprotegerin in E. coli

In the example, the expression vector used was pAMG21, a derivative of pCFM1656 (ATCC accession no. 69576) which contains appropriate restriction sites for insertion of genes downstream from the lux PR promoter. (See U.S. Pat. No. 5,169,318 for description of the lux expression system). The host cell used was GM120. This host has the lacI$^Q$ promoter and laci gene integrated into a second site in the host chromosome of a prototrophic E. coli K12 host. Other commonly used E. coli expression vectors and host cells are also suitable for expression.

A DNA sequence coding for an N-terminal methionine and amino acids 32–401 of the human Osteoprotegerin polypeptide was placed under control of the luxPR promoter in the plasmid expression vector pAMG21 as follows. To accomplish this, PCR using oligonucleotides #1257-20 and #1257-19 as primers was performed using as a template plasmid pRcCMV-huCrl containing the human Osteoprotegerin cDNA and thermocycling for 30 cycles with each cycle being: 94° C. for 20 seconds, followed by 37° C. for 30 seconds, followed by 72° C. for 30 seconds. The resulting PCR sample was resolved on an agarose gel, the PCR product was excised, purified, and restricted with KpnI and BamHI restriction endonucleases and purified.

Synthetic oligonucleotides #1257-21 and #1257-22 were phoph-orylated individually using T4 polynucleotide kinase and ATP, and were then mixed together, heated at 94° C. and allowed to slow cool to room temperature to form an oligonucleotide linker duplex containing NdeI and KpnI sticky ends.

The phosphorylated linker duplex formed between oligonucleotides #1257-21 and #1257-22 containing NdeI and KpnI cohesive ends (see diagram below) and the KpnI and BamHI digested and purified PCR product generated using oligo primers #1257-20 #1257-19 (see above) was directionally inserted between two sites of the plasmid vector pAMG21, namely the NdeI site and BamHI site, using standard recominant DNA methodology (see diagram and sequences below). The synthetic linker utilized *E. coli* codons and provided for a N-terminal methionine.

Two clones were selected and plasmid DNA isolated, and the human Osteoprotegerin insert was subsequently DNA sequence confirmed. The resulting pAMG21 plasmid containing amino acids 32–401 of the human Osteoprotegerin polypeptide immediately preceeded in frame by a methionine is here to referred to as pAMG21-hu-Osteoprotegerin-32-401 or pAMG21-huCrl-32-401

Oligo#1257-19

5'-TACGCACTGGATCCTTATAAGCAGCT-
        TATTTTTACTGATTGGAC-3'      (SEQ ID NO: 36)

Oligo#1257-20

5'-GTCCTCCTGGTACCTACCTAAAACAAC-3'(SEQ ID NO: 37)

Oligo#1257-21

5'-TATGGATGAAGAAACTTCTCATCAGCT-
        GCTGTGTGATAAATGTCCGCCGGGTAC-3(SEQ ID NO: 38)

Oligo#1257-22

5' CCGGCGGACATTTATCACACAGCAGCT-
        GATGAGAAGTTTCTTCATCCA-3'      (SEQ ID NO: 39)

Cultures of pAMG21-hu-Osteoprotegerin-32-401 in *E. coli* GM120 in 2XYT media containing 20 ug/ml kanamycin were incubated at 30° C. prior to induction. Induction of huCrl-co-DN10 gene product expression from the luxPR promoter was achieved following the addition of the synthetic autoinducer N-(3-oxohexanoyl)-DL-homoserine lactone to the culture media to a final concentration of 30 ng/ml and cultures were incubated at either 30° C. or 37° C. for a further 6 hours. After 6 hours, the bacterial cultures were examined by microscopy for the presence of inclusion bodies and were then pelletted by centrifugation. Refractile inclusion bodies were observed in induced cultures indicating that some of the recombinant hu-Osteoprotegerin-32-401 gene product was produced insolubly in *E. coli*. Some bacterial pellets were resuspended in 10 mM Tris-HCl/pH8, 1 mM EDTA and lysed directly by addition of 2×Laemalli sample buffer to 1×final, and b-mercaptoethanol to 5% final concentration, and analyzed by SDS-PAGE. A substantially more intense coomassie stained band of approximately 42 kDa was observed on a SDS-PAGE gel containing total cell lysates of 30° C. and 37° C. induced cultures versus lane 2 which is a total cell lysate of a 30° C. uninduced culture. The expected gene product would be 370 amino acids in length and have an expected molecular weight of about 42.2 kDa. Following induction at 37° C. for 6 hours, an additional culture was pelletted and either processed for isolation of inclusion bodies (see below) or processed by microfluidizing. The pellet processed for microfluidizing was resuspended in 25 mM Tris-HCl/pH8, 0.5 M NaCl buffer and passed 20 times through a Microfluidizer Model 1108 (Microfluidics Corp.) and collected. An aliquot was removed of the collected sample (microfluidized total lysate), and the remainder was pelletted at 20,000×g for 20 minutes.

The supernatant following centrifugation was removed (microfluidized soluble fraction) and the pellet resuspended in a 25 mM Tris-HCl/pH8, 0.5 M NaCl, 6 M urea solution (microfluidized insoluble fraction). To an aliquot of either the total soluble, or insoluble fraction was added to an equal volume of 2×Laemalli sample buffer and -βmercaptoethanol to 5% final concentration. The samples were then analyzed by SDS-PAGE. A significant amount of recombinant hu-Osteoprotegerin-32-401 gene product appeared to be found in the insoluble fraction. To purify the recombinant protein inclusion bodies were purified as follows:

Bacterial cells were separated from media by density gradient centrifugation in a Beckman J-6B centrifuge equipped with a JS-4.2 rotor at 4,900×g for 15 minutes at 4° C. The bacterial pellet was resuspended in 5 ml of water and then diluted to a final volume of 10 ml with water. This suspension was transferred to a stainless steel cup cooled in ice and subjected to sonic disruption using a Branson Sonifier equipped with a standard tip (power setting=5, duty cycle=95%, 80 bursts). The sonicated cell suspension was centrifuged in a Beckman Optima TLX ultracentrifuge equipped with a TLA 100.3 rotor at 195,000 ×g for 5 to 10 minutes at 23° C. The supernatant was discarded and the pellet rinsed with a stream of water from a squirt bottle. The pellets were collected by scraping with a micro spatula and transferred to a glass homogenizer (15 ml capacity). Five ml of Percoll solution (75% liquid Percoll, 0.15 M sodium chloride) was added to the homogenizer and the contents are homogenized until uniformly suspended. The volume was increased to 19.5 ml by the addition of Percoll solution, mixed, and distributed into 3 Beckman Quick-Seal tubes (13×32 mm). Tubes were sealed according to manufacturers instructions. The tubes were spun in a Beckman TLA 100.3 rotor at 23° C., 20,000 rpm (21,600×g), 30 minutes. The tubes were examined for the appropriate banding pattern. To recover the refractile bodies, gradient fractions were recovered and pooled, then diluted with water. The inclusion bodies were pelleted by centrifugation, and the protein concentration estimation following SDS-PAGE.

An aliquot of inclusion bodies isolated as described below was dissolved into 1×Laemalli sample buffer +5% b-mercaptoethanol and resolved on a SDS-PAGE gel and the isolated inclusion bodies provide a highly purified recombinant hu-Osteoprotegerin-32-401 gene product. The major ~42 kDa band observed after resolving inclusion bodies on a SDS-polyacrylamide gel was excised from a separate gel and the N-terminal amino acid sequence determined essentially as described (Matsudaira et al. J. Biol. Chem. 262, 10–35 (1987)). The following sequence was determined after 19 cycles (SEQ ID NO: 40):

$NH_2$—MYDEETSHQLLCDKCPPGT—COOH

This sequence was found to be identical to the first 19 amino acids encoded by the pAMG21-hu-osteoprotegerin-32-401 expression vector, produced by a methionine residue provided by the bacterial expression vector.

While the invention has been described in what is considered to be its preferred embodiments, it is not to be limited to the-disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An isolated nucleic acid encoding a polypeptide having the biological activity of inhibiting bone resorption and comprising a derivative of the amino acid sequence 22 to 401 as shown in FIG. 9B (SEQ ID NO:6) which differs from amino acid residues 22 to 401 of SEQ ID NO:6 by deletion or carboxy-terminal truncation of part or all of amino acid residues 180 to 401.

2. An isolated nucleic acid encoding a polypeptide having the biological activity of inhibiting bone resorption and comprising a derivative of the amino acid sequence 1 to 401 as shown in FIG. 9B (SEQ ID NO:6) which differs from amino acid residues 1 to 401 of SEQ ID NO:6 by deletion or carboxy-terminal truncation of part or all of amino acid residues 180 to 401.

3. An isolated nucleic acid encoding a polypeptide having the biological activity of inhibiting bone resorption and comprising a derivative of the amino acid sequence 22 to 401 as shown in either FIG. 2B (SEQ ID NO:2) or 9A (SEQ ID NO:4) which differs from amino acid residues 22 to 401 of SEQ ID NO:2 or SEQ ID NO:4 by deletion or carboxy-terminal truncation of part or all of amino acid residues 180 to 401.

4. An isolated nucleic acid encoding a polypeptide having the biological activity of inhibiting bone resorption and comprising a derivative of the amino acid sequence 1 to 401 as shown in either FIG. 2B (SEQ ID NO:2) or 9A (SEQ ID NO:4) which differs from amino acid residues 1 to 401 of SEQ ID NO:2 or SEQ ID NO:4 by deletion or carboxy-terminal truncation of part or all of amino acid residues 180 to 401.

5. The nucleic acid of any of claims 1–4 which is cDNA, genomic DNA, synthetic DNA or RNA.

6. The nucleic acid of any of claim 1–4 wherein one or more of the codons are modified for E.coli expression.

7. The nucleic acid of any of claims 1–4 having a detectable label attached thereto.

8. The nucleic acid of claims 1 or 3 wherein the polypeptide further comprises an additional amino terminal methionine residue.

9. The nucleic acid of claims Korfwherein the polypeptide is fused to an Fc region of human IgG or to a derivative of an Fc region of human IaG.

10. An expression vector comprising the nucleic acids of any of claims 1–4.

11. An isolated host cell transformed or transfected with the expression vector of claim 10.

12. The host cell of claim 11 which is a eucaryotic host cell.

13. The host cell of claim 12 which is selected from the group consisting of CHO, COS, 293, 3T3, CV-1 and BHK cells.

14. The host cell of claim 11 which is a procaryotic host cell.

15. The host cell of claim 11 which is *Escherichia coli*.

16. A process for the production of a polypeptide having the biological activity of specifically increasing bone density, the process comprising:

growing under suitable nutrient conditions host cells transformed or transfected with the nucleic acids of any of claims 1 to 4; and isolating the polyeptide products of the expression of the nucleic acids.

\* \* \* \* \*

UNITED STATES PATENT AND TRADEMARK OFFICE
CERTIFICATE OF CORRECTION

PATENT NO. : 6,284,485 B1
DATED : September 4, 2001
INVENTOR(S) : Boyle et al.

It is certified that error appears in the above-identified patent and that said Letters Patent is hereby corrected as shown below:

Column 1,
Line 46, change "TNFa" to -- TNFα --
Line 47, change "27" to -- 267 --
Line 52, change "5" to -- 57 --
Line 61, insert -- 75 -- after "Cell"

Column 2,
Line 9, change "TNFA" to -- TNFα --

Column 6,
Lines 1, 6 and 10, change "Manassa" to -- Manassas --

Column 9,
Line 52, change "Reminaton's" to -- Remington's --

Column 11,
Line 37, change "TNFβ" to -- TNFα --

Column 12,
Ine 30, change "PMOB" to -- pMOB --

Column 13,
Line 8, change "18" to -- 183 --

Column 15,
Line 29, change "21" to -- 82 --
Line 57, change "1" to -- 152 --
Line 61, change "15" to -- 152 --

Column 18,
Line 26, change "-94%" to -- ~94% --
Line 38, change "255" to -- 25 --

UNITED STATES PATENT AND TRADEMARK OFFICE
CERTIFICATE OF CORRECTION

PATENT NO. : 6,284,485 B1
DATED : September 4, 2001
INVENTOR(S) : Boyle et al.

It is certified that error appears in the above-identified patent and that said Letters Patent is hereby corrected as shown below:

Column 19,
Line 5, change "-90%" to -- ~90% --
Line 15, change "Pecombinant" to -- Recombinant --

Column 20,
Line 12, change "26" to -- 262 --
Line 38, change "laci" to -- lacI --

Column 68,
Line 62, change "Korfwherein" to -- 1 or 3 wherein --

Column 69,
Line 10, change "11" to -- 14 --

Signed and Sealed this

Sixth Day of August, 2002

Attest:

JAMES E. ROGAN
Attesting Officer  Director of the United States Patent and Trademark Office